(12) United States Patent
Kai et al.

(10) Patent No.: US 8,227,798 B2
(45) Date of Patent: Jul. 24, 2012

(54) COMPOUND FOR ORGANIC ELECTROLUMINESCENT DEVICE AND ORGANIC ELECTROLUMINESCENT DEVICE

(75) Inventors: Takahiro Kai, Kitakyushu (JP);
Toshihiro Yamamoto, Kitakyushu (JP);
Masanori Hotta, Kitakyushu (JP);
Junya Ogawa, Kitakyushu (JP)

(73) Assignee: Nippon Steel Chemical Co., Ltd., Tokyo (JP)

( * ) Notice: Subject to any disclaimer, the term of this patent is extended or adjusted under 35 U.S.C. 154(b) by 347 days.

(21) Appl. No.: 12/593,126

(22) PCT Filed: Mar. 24, 2008

(86) PCT No.: PCT/JP2008/055419
§ 371 (c)(1),
(2), (4) Date: Sep. 25, 2009

(87) PCT Pub. No.: WO2008/123189
PCT Pub. Date: Oct. 16, 2008

(65) Prior Publication Data
US 2010/0044695 A1  Feb. 25, 2010

(30) Foreign Application Priority Data

Mar. 26, 2007  (JP) .................................. 2007-079414

(51) Int. Cl.
*H01L 35/24* (2006.01)
(52) U.S. Cl. .................................. 257/40; 257/E51.001
(58) Field of Classification Search .................... 257/40, 257/E51.001
See application file for complete search history.

(56) References Cited

U.S. PATENT DOCUMENTS
3,843,649 A  10/1974  Seltzer et al.
(Continued)

FOREIGN PATENT DOCUMENTS
EP  1956022 A1  8/2008
(Continued)

OTHER PUBLICATIONS

Ehlers et al., "Some Ethers and Amino-Derivatives of s-Triazine," Journal of Chemical and Engineering Data, 1964, vol. 9, No. 1, pp. 110-111, Chemical Abstracts, 1964, vol. 60, 8033b, CA Abstracts No. 60:45735.
(Continued)

*Primary Examiner* — Anthony Ho
(74) *Attorney, Agent, or Firm* — Birch, Stewart, Kolasch & Birch, LLP

(57) ABSTRACT

Disclosed is an organic electroluminescent device (organic EL device) which is improved in luminous efficiency, fully secured of driving stability, and of simple constitution. Also disclosed is a compound useful for the fabrication of said organic EL device. The organic electroluminescent device comprises organic layers including a light-emitting layer disposed between an anode and a cathode which are piled one upon another on a substrate and said organic layers comprise a compound represented by general formula (1). A light-emitting layer containing a phosphorescent dopant is suitable for an organic layer comprising a compound represented by general formula (1). In general formula (1), X is CR or N; $Ar_1$ to $Ar_3$ each is a substituted or unsubstituted aromatic hydrocarbon group or a substituted or unsubstituted aromatic heterocyclic group; $Ar_2$, $Ar_3$ and the nitrogen to which $Ar_2$ and $Ar_3$ are joined may together form a nitrogen-containing heterocyclic ring; m and n each is an integer of 1 or 2 and the sum of m and n is 3.

(1)

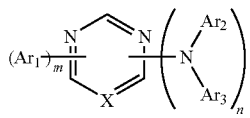

8 Claims, 1 Drawing Sheet

U.S. PATENT DOCUMENTS

| | | | |
|---|---|---|---|
| 6,512,082 B2 * | 1/2003 | Towns et al. | 528/394 |
| 2001/0037012 A1 | 11/2001 | Towns et al. | |
| 2003/0194577 A1 | 10/2003 | Towns et al. | |
| 2005/0127823 A1 * | 6/2005 | Iwakuma et al. | 313/504 |
| 2005/0221124 A1 * | 10/2005 | Hwang et al. | 428/690 |
| 2007/0296328 A1 | 12/2007 | Matsuura et al. | |

FOREIGN PATENT DOCUMENTS

| | | |
|---|---|---|
| EP | 2080762 A1 | 7/2009 |
| JP | 49-54387 A | 5/1974 |
| JP | 2004-500455 A | 1/2004 |
| JP | 2005-186607 A | 7/2005 |
| JP | 2006-80271 A | 3/2006 |
| JP | 2007-77033 A | 3/2007 |
| JP | 2007-180147 A | 7/2007 |
| WO | WO-03/078541 A1 | 9/2003 |
| WO | WO-2005/076668 A1 | 8/2005 |
| WO | WO-2007/063754 A1 | 6/2007 |
| WO | WO-2008/056746 A1 | 5/2008 |

OTHER PUBLICATIONS

Fang et al. "Synthesis and Properties of a New Poly(arylene ethynylene) Containing 1,3,5-Triazine Units," Macromolecular Chemistry and Physics, 2004, vol. 205, No. 6, pp. 795-800.

* cited by examiner

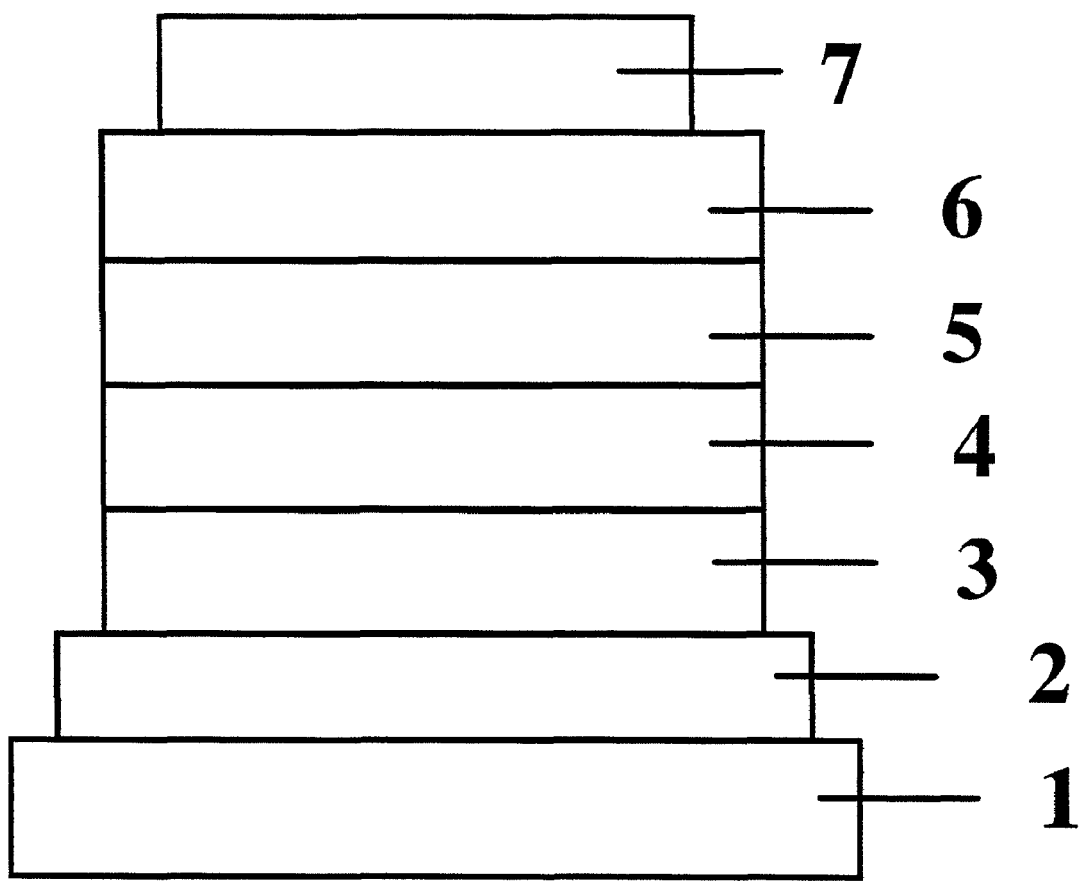

COMPOUND FOR ORGANIC ELECTROLUMINESCENT DEVICE AND ORGANIC ELECTROLUMINESCENT DEVICE

FIELD OF TECHNOLOGY

This invention relates to a novel compound for an organic electroluminescent device and to an organic electroluminescent device (hereinafter referred to as organic EL device) using said compound.

BACKGROUND TECHNOLOGY

An organic electroluminescent device (hereinafter referred to as organic EL device) in the simplest structure is generally constituted of a light-emitting layer sandwiched between a pair of counter electrodes and functions by utilizing the following phenomenon. Upon application of an electrical field between the electrodes, electrons are injected from the cathode and holes are injected from the anode and they recombine in the light-emitting layer with emission of light.

In recent years, organic thin films have been used in the development of organic EL devices. In particular, in order to enhance the luminous efficiency, the kind of electrodes has been optimized for the purpose of improving the efficiency of injecting carriers from the electrodes and a device has been developed in which a hole-transporting layer of an aromatic diamine and a light-emitting layer of 8-hydroxyquinoline aluminum complex (hereinafter referred to as Alq3) are disposed in thin film between the electrodes. This device has brought about a marked improvement in the luminous efficiency over the conventional devices utilizing single crystals of anthracene and the like and thereafter the developmental works of organic EL devices have been focused on commercial applications to high-performance flat panels featuring self-luminescence and high-speed response.

In another effort to enhance the luminous efficiency of the device, the use of phosphorescence in place of fluorescence is investigated. The aforementioned device comprising a hole-transporting layer of an aromatic diamine and a light-emitting layer of Alq3 and many other devices utilize fluorescence. The use of phosphorescence, that is, emission of light from the excited triplet state is expected to enhance the luminous efficiency approximately three to four times that of the conventional devices utilizing fluorescence (emission of light from the excited singlet state). To achieve this objective, the use of coumarin derivatives and benzophenone derivatives in the light-emitting layer has been investigated, but these compounds merely produced luminance at an extremely low level. Thereafter, europium complexes were tried to utilize the excited triplet state, but failed to emit light at high efficiency. In recent years, as is mentioned in the patent document 1, a large number of researches are conducted with the objective of enhancing the luminous efficiency and extending the service life while mainly utilizing organic metal complexes such as iridium complexes.

Patent document 1: JP2003-515897 A
Patent document 2: JP2001-313178 A
Patent document 3: JP2006-76901 A
Patent document 4: WO2005-76668 A
Patent document 5: WO2003-78541 A Non-patent document 1: Applied Physics Letters, 2003, 83, 569-571
Non-patent document 2: Applied Physics Letters, 2003, 82, 2422-2424

A host material to be used with the aforementioned dopant material becomes important in order to enhance the luminous efficiency. Of host materials proposed thus far, a typical example is 4,4'-bis(9-carbazolyl)biphenyl (hereinafter referred to as CBP) presented in the patent document 2. CBP exhibits relatively good luminous characteristics when used as a host material for green phosphorescent emitters, typically tris(2-phenylpyridine)iridium (hereinafter referred to as Ir(ppy)3). On the other hand, CBP fails to perform with sufficient luminous efficiency when used as a host material for blue phosphorescent emitters. This is because the energy level of the lowest triplet excited state of CBP is lower than that of common blue phosphorescent emitters and the triplet excitation energy of a blue phosphorescent emitter in use is transferred to CBP. That is to say, if a phosphorescent host material were designed to have triplet excitation energy higher than that of a phosphorescent emitter, the triplet excitation energy of said phosphorescent emitter would be confined effectively and, as a result, the luminous efficiency would be enhanced. With the objective of improving this energy-confining effect, the triplet excitation energy is increased by modifying the structure of CBP in the non-patent document 1 and the luminous efficiency of bis[2-(4,6-difluorophenyl)pyridinato-N,C2']iridium picolinate (hereinafter referred to as Flrpic) is improved by this means. Similarly, the luminous efficiency is enhanced by using 1,3-dicarbazolylbenzene (hereinafter referred to as mCP) as a host material in the non-patent document 2. However, these host materials are not satisfactory in practical use, particularly from the viewpoint of durability.

Moreover, the host material needs to have the balanced electrical charge (hole and electron) injection/transport characteristics in order to enhance the luminous efficiency. The electron transport property is inferior to the hole transport property in the case of CBP and this disturbs the balance of electrical charges in the light-emitting layer and causes excess holes to flow out to the side of the cathode thereby reducing the probability of recombination of holes and electrons in the light-emitting layer and decreasing the luminous efficiency. Furthermore, occurrence of the recombination is limited to a narrow region in the vicinity of the interface on the cathode side in this case. Therefore, in the case where an electron-transporting material like Alq3 whose energy level of the lowest triplet excited state is lower than that of Ir(ppy)3 is used, there may also arise the possibility that the luminous efficiency may decrease due to transfer of the triplet excitation energy from the dopant to the electron-transporting material.

One of the means to prevent holes from flowing out to the electron-transporting layer is to provide a hole-blocking layer between the light-emitting layer and the electron-transporting layer. This hole-blocking layer accumulates holes efficiently in the light-emitting layer and contributes to improve the probability of recombination of holes and electrons in the light-emitting layer and enhance the luminous efficiency (the patent document 2). Hole-blocking materials in general use include 2,9-dimethyl-4,7-diphenyl-1,10-phenanthroline (hereinafter referred to as BCP) and p-phenylphenolato-bis (2-methyl-8-quinolinolato)aluminum (hereinafter referred to as BAlq). These materials can prevent holes from flowing out of the light-emitting layer to the electron-transporting layer; however, the lowest energy level of the excited triplet state of both of them is lower than that of a phosphorescent dopant such as Ir(ppy)3 and sufficient luminous efficiency cannot be obtained.

Moreover, BCP tends to crystallize even at room temperature and lacks reliability as a hole-blocking material and the life of the device is extremely short. Although BAlq is reported to have a Tg of approximately 100° C. and provide the device with relatively good life, its hole-blocking ability is not enough.

The aforementioned examples indicate that, in order for organic EL devices to perform at high luminous efficiency, a host material is required to have high triplet excitation energy and to be balanced in the electrical charge (hole and electron) injection/transport characteristics. Furthermore, the host material is hopefully a compound endowed with electrochemical stability, high heat resistance, and excellent stability in the amorphous state. However, no compound capable of satisfying these properties on a practical level has been known at the present time.

Attempts have been made to introduce a skeleton that has an excellent hole transport property as represented by a triarylamine or carbazole and another skeleton that has an excellent electron transport property as represented by pyrimidine or triazine into one and the same molecule.

The following compounds are disclosed in the patent document 3.

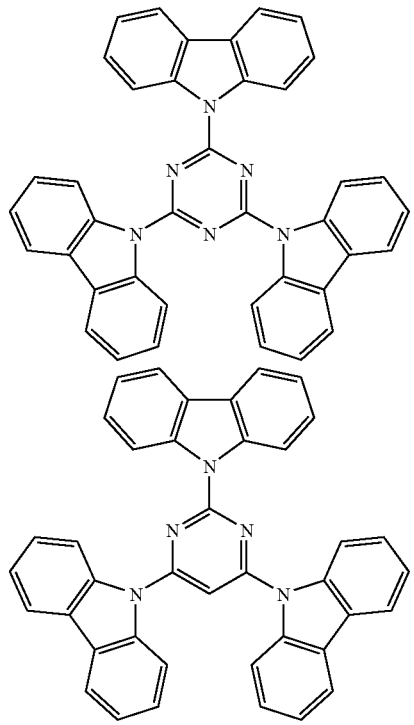

In these compounds, the lowest unoccupied molecular orbital (LUMO) extends over the triazine ring or the pyrimidine ring at the center of the molecule and the periphery of the LUMO is enveloped in the carbazole skeletons wherein the highest occupied molecular orbital (HOMO) extends. The LUMO is thus centralized and confined inside the molecule and this arrangement acts against the movement of electrons between molecules and, further, it necessitates improvement in stability when the molecule is subjected to one-electron reduction.

Moreover, the following compounds are disclosed in the patent documents 4 and 5.

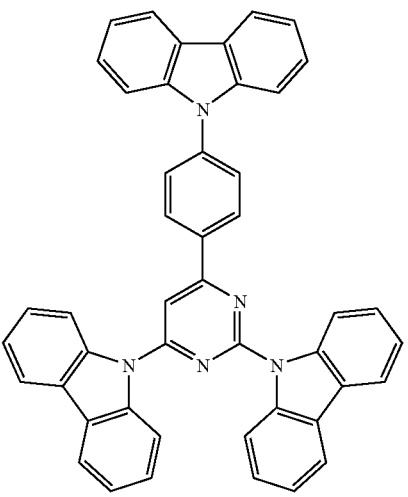

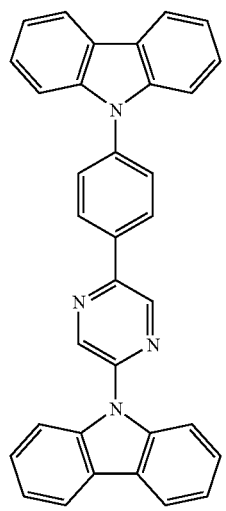

In these compounds too, the LUMO extends over the two rings consisting of the benzene ring and the pyrimidine ring at the center of the molecule and the periphery of the LUMO is enveloped in the carbazole skeletons wherein the HOMO extends. That is, the LUMO is confined inside the molecule and this arrangement acts against the movement of electrons between molecules. Furthermore, in these compounds, bonding of the carbazolyl group to the benzene ring lowers the triplet excitation energy. Therefore, depending upon the triplet energy level of the dopant in use, the triplet excitation energy of the dopant is transferred to the host molecule and this makes it impossible to obtain high luminous efficiency.

Further, the following compounds are given as examples in the patent document 5.

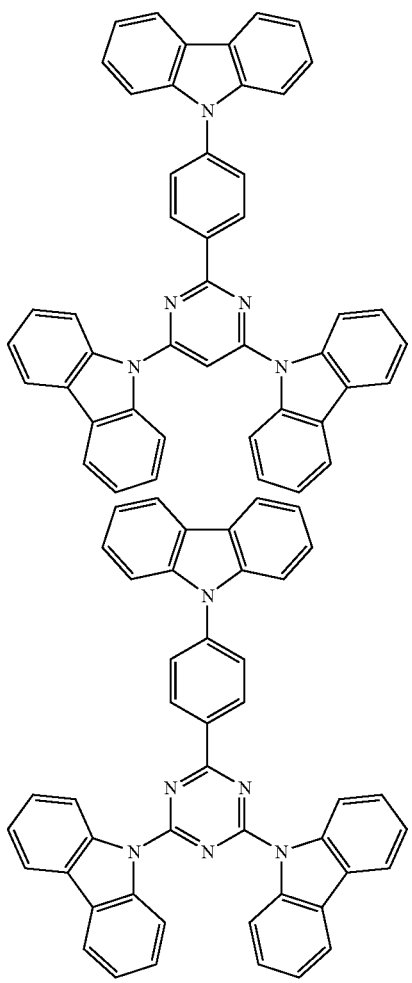

In these compounds too, the LUMO is centralized on the two rings, either on the benzene ring and the pyrimidine ring or on the benzene ring and the triazine ring, at the center of the molecule and the periphery of the LUMO is enveloped in the carbazole skeletons wherein the HOMO extends. That is, confinement of the LUMO inside the molecule acts against the movement of electrons between molecules. In these compounds too, bonding of the carbazolyl group to the benzene ring lowers the triplet excitation energy. In consequence, depending upon the triplet energy level of the dopant in use, the triplet excitation energy is transferred to the host molecule and this makes it impossible to obtain high luminous efficiency.

When a plurality of skeletons differing from one another in the electrical charge transport properties are introduced into one and the same molecule, the molecule may undergo large changes in the balance of electrical charges and in the stability depending upon the method used for the introduction. This indicates that the use of a molecule of this kind particularly as a host material is bound to affect vitally the luminous characteristics and life of the device and necessitates further improvements when practical use is intended.

DISCLOSURE OF THE INVENTION

Problems to be Solved by the Invention

In applications of organic EL devices to display devices such as flat panel displays, it is necessary to improve the luminous efficiency of the device and, at the same time, to fully secure the driving stability of the device. Under the aforementioned circumstances, a theme of this invention is to provide an organic EL device that performs at high efficiency with good driving stability and is practically useful and to provide a compound suitable therefor.

Means to Solve the Problems

The inventors of this invention have found that the aforementioned problems can be solved by using a compound of specified structure for an organic EL device and completed this invention.

Accordingly, this invention relates to a compound for an organic electroluminescent device which comprises a compound represented by general formula (1):

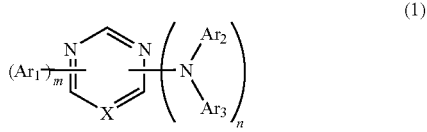

wherein
X is a substituted or unsubstituted methine group or a nitrogen,
$Ar_1$ to $Ar_3$ each is independently a substituted or unsubstituted aromatic hydrocarbon group or a substituted or unsubstituted aromatic heterocyclic group,
$Ar_2$, $Ar_3$, and the nitrogen to which $Ar_2$ and $Ar_3$ are joined may together form a nitrogen-containing heterocyclic ring,
m and n each is an integer of 1 or 2 and the sum of m and n is 3.

A preferable example of the compounds for an organic electroluminescent device represented by the aforementioned general formula (1) is a compound for an organic electroluminescent device represented by the following general formula (2).

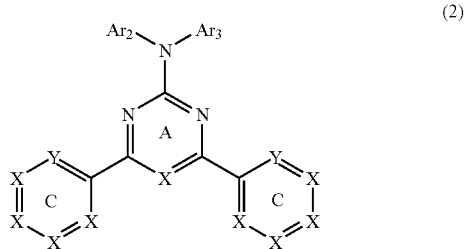

In general formula (2), X is independently a substituted or unsubstituted methine group or a nitrogen, Y is a substituted or unsubstituted methine group, $Ar_2$ and $Ar_3$ each is independently a substituted or unsubstituted aromatic hydrocarbon group or a substituted or unsubstituted aromatic heterocyclic group, and $Ar_2$, $Ar_3$, and the nitrogen to which $Ar_2$ and $Ar_3$ are joined may together form a nitrogen-containing heterocyclic ring.

A compound preferable for an organic electroluminescent device is provided when $Ar_2$ and $Ar_3$ each is independently a phenyl group, a naphthyl group, a phenanthryl group, a pyridyl group, a pyrimidyl group, or a triazyl group or when —$NAr_2Ar_3$ is an N-carbazolyl group, an N-phenoxazinyl group, an N-phenothiazinyl group, or an N-β-carbolinyl group in general formula (1) or (2).

Furthermore, a preferable compound for an organic electroluminescent device is provided when one or more of the following conditions are satisfied in general formula (2): X and Y constituting ring C each is a substituted or unsubstituted methine group; ring C is an unsubstituted aromatic hydrocarbon group or an unsubstituted aromatic heterocyclic group; X constituting ring A is a nitrogen; and X is an unsubstituted methine group.

Still further, this invention relates to an organic electroluminescent device comprising an organic layer containing the aforementioned compound for an organic electroluminescent device. Here, a preferable organic electroluminescent device is provided when the aforementioned organic layer is at least one layer selected from a light-emitting layer, a hole-transporting layer, an electron-transporting layer, and a hole-blocking layer or the aforementioned organic layer is a light-emitting layer containing a phosphorescent dopant.

BRIEF DESCRIPTION OF THE DRAWING

FIG. 1 schematically shows the cross section of an example of an organic EL device.

Explanation of symbols: 1 substrate; 2 anode; 3 hole-injecting layer; 4 hole-transporting layer; 5 light-emitting layer; 6 electron-transporting layer; 7 cathode.

The mode of reduction to practice of this invention will be described in detail below.

A compound for an organic EL device according to this invention (hereinafter referred to as compound of this invention) has excellent electron transport properties and hole transport properties and shows extremely high durability against one-electron oxidation and one-electron reduction. These characteristics are due to the structural feature of the compound and will be described in detail below.

The compound of this invention is represented by the aforementioned general formula (1) or (2). As general formula (1) includes general formula (2), general formula (1) represents general formula (2) wherever any subject common to the two general formulas is explained. The common symbols in general formulas (1) and (2) have the same meaning. The structural feature of a compound represented by general formula (1) is, firstly, arrangement of a pyrimidine ring or a triazine ring, which has an electron injection/transport property, at the center of the molecule. Secondly, for the purpose of improving this electron injection/transport property, one $Ar_1$ or two $Ar_1$s are bonded directly to the pyrimidine ring or the triazine ring. Furthermore, for the purpose of improving the hole injection/transport property, one $NAr_2Ar_3$ or two $NAr_2Ar_3$s are bonded directly to the pyrimidine ring or the triazine ring. Turning attention to the frontier orbital of the compound obtained in this manner, the LUMO extends over the region formed by the six-membered heterocyclic ring at the center and $Ar_1$ while the HOMO extends over $NAr_2Ar_3$. As both LUMO and HOMO extend over the region formed by a plurality of aromatic rings, holes and electrons are delocalized to maintain the molecule in a stable condition even when the molecule is subjected to one-electron oxidation or one-electron reduction. Furthermore, both orbitals project out of the molecule widely and this facilitates the movement of electrical charges between molecules and, as a result, the transport properties of electrons and holes are well balanced.

More preferable among the compounds represented by general formula (1) are compounds represented by the aforementioned general formula (2) and they are more pronounced in the aforementioned structural feature.

In general formula (2), the LUMO extends over the region formed by ring A and two ring Cs. Further, when X and Y on ring C are substituted methine groups, the substituents are selected preferably in such a manner as to extend the LUMO. It follows as a consequence that the LUMO extends over the region centering around ring A and two ring Cs and this helps to improve the electron transport property and increase the stability when the molecule is subjected to one-electron reduction.

On the other hand, the HOMO is distributed over $NAr_2Ar_3$ and the extension of the HOMO in a manner of projecting out of the molecule acts advantageously for the movement of holes between molecules. In particular, when $Ar_2$, $Ar_3$, and the nitrogen to which $Ar_2$ and $Ar_3$ are joined form together a nitrogen-containing heterocyclic ring, the planarity of the HOMO increases. A molecule such as this maintains its stability by the delocalization effect when subjected to one-electron oxidation.

In general formulas (1) and (2), $Ar_1$, $Ar_2$, and $Ar_3$ each is independently a substituted or unsubstituted aromatic hydrocarbon group or a substituted or unsubstituted aromatic heterocyclic group. Moreover, it is preferable that $Ar_2$ and $Ar_3$ that are joined to the same nitrogen may form a nitrogen-containing heterocyclic ring with said nitrogen.

Preferable examples of the unsubstituted aromatic hydrocarbon groups include groups that are formed by taking one H away respectively from benzene, naphthalene, phenanthrene, and pyrene. Preferable examples of the unsubstituted aromatic heterocyclic groups include groups that are formed by taking one H away respectively from pyridine, pyrimidine, triazine, pyrazine, pyridazine, quinoline, isoquinoline, quinoxaline, and naphthyridine.

In the case where the aforementioned aromatic hydrocarbon groups or aromatic heterocyclic groups are substituted, preferable examples of the substituents include aromatic hydrocarbon groups and aromatic heterocyclic groups such as a phenyl group, a naphthyl group, a biphenylyl group, a pyridyl group, a pyrimidinyl group, a triazinyl group, a pyrazinyl group, a pyridazinyl group, a quinolyl group, an isoquinolyl group, a quinoxalinyl group, and a naphthyridinyl group. Preferred are six-membered aromatic groups such as a phenyl group, a biphenylyl group, a pyridyl group, a pyrimidinyl group, a triazinyl group, a pyrazinyl group, and a pyridazinyl group.

In the case where the aforementioned substituent is joined to the adjoining carbons, said substituent may form a condensed ring with $Ar_2$ or $Ar_3$. In this case, examples of the condensed rings containing $Ar_2$ or $Ar_3$ include aromatic hydrocarbons and aromatic heterocyclic compounds such as naphthalene, phenanthrene, quinoline, isoquinoline, phthalazine, naphthyridine, quinoxaline, quinazoline, carbazole, phenanthridine, acridine, phenanthroline, and phenazine.

In the case where $Ar_2$, $Ar_3$, and the nitrogen to which they are joined form a nitrogen-containing heterocyclic ring, preferable examples of such heterocyclic rings include carbazole, phenoxazine, phenothiazine, and β-carboline.

In general formulas (1) and (2), X is a substituted or unsubstituted methine group or a nitrogen. The unsubstituted methine group is expressed by —CH— and the substituted methine group by —CR—. Here, preferable examples of the substituent R in the substituted methine group include aromatic hydrocarbon groups and aromatic heterocyclic groups such as a phenyl group, a naphthyl group, a biphenylyl group, a pyridyl group, a pyrimidinyl group, a triazinyl group, a pyrazinyl group, a pyridazinyl group, a quinolyl group, an isoquinolyl group, a quinoxalinyl group, and a naphthyridinyl group. Preferred are six-membered aromatic groups such as a phenyl group, a biphenylyl group, a pyridyl group, a pyrimidinyl group, a triazinyl group, a pyrazinyl group, and a pyridazinyl group.

In the case where Xs located in the adjoining positions in ring C in general formula (2) are substituted methine groups, the substituents on Xs may join together to form a condensed ring containing ring C. Examples of the condensed rings containing ring C include aromatic carbocyclic rings and aromatic heterocyclic rings such as naphthalene, phenanthrene, quinoline, isoquinoline, phthalazine, naphthyridine, quinoxaline, quinazoline, carbazole, phenanthridine, acridine, phenanthroline, and phenazine.

In general formula (2), X constituting ring C is preferably an unsubstituted methine group or a nitrogen. Moreover, X and Y each is preferably a substituted or unsubstituted methine group and, where X and Y are substituted methine groups, the substituents are preferably six-membered aromatic groups.

In general formula (1), m and n each is an integer of 1 or 2 and the sum of m and n is 3. Therefore, of the constituents of a six-membered ring, three carbons other than two nitrogens and X respectively have substituents, either $Ar_1$ or $NAr_2Ar_3$. As the compounds represented by general formula (2) are preferable examples of the compounds represented by general formula (1), it is to be understood that the six-membered ring in general formula (1) corresponds to ring A in general formula (2), $NAr_2Ar_3$ in general formula (1) corresponds to $NAr_2Ar_3$ in general formula (2), and $Ar_1$ in general formula (1) corresponds to ring C in general formula (2).

The synthesis of the compounds of this invention can be performed, for example, by the following synthetic routes.

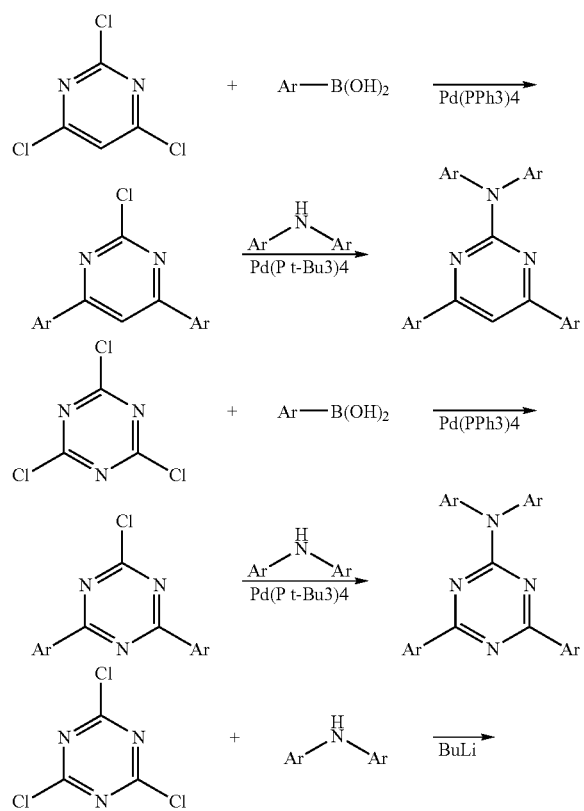

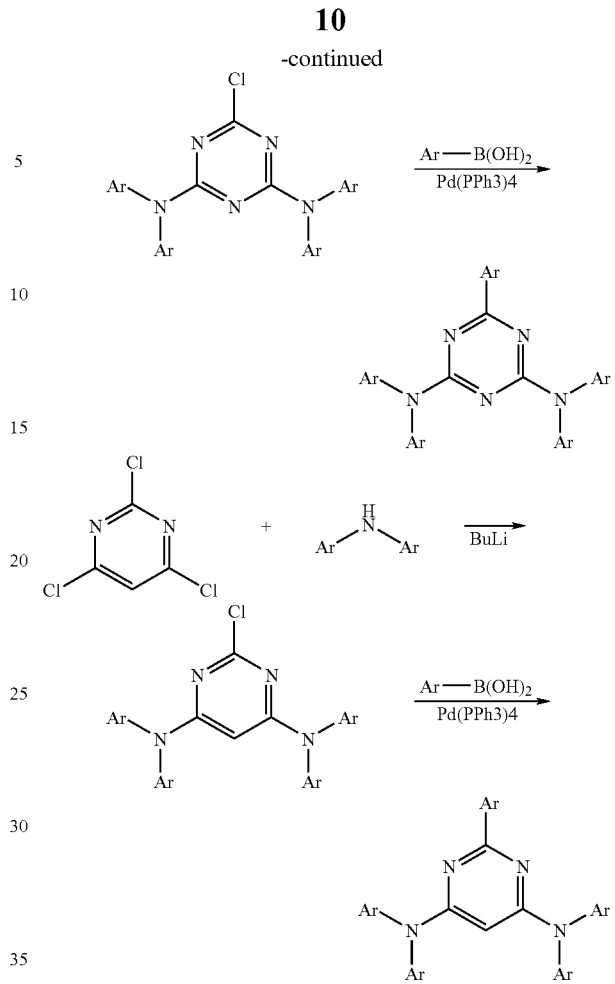

The compound of this invention is obtained by the hetero-coupling reaction of a halogenated triazine derivative or a halogenated pyrimidine derivative with an aniline derivative or a boronic acid derivative in the presence of a palladium catalyst or a copper catalyst. The halogen atoms include chlorine, bromine, and iodine. A solvent capable of dissolving the raw materials may be used for the reaction; for example, toluene, xylene, dioxane, tetralin, quinoline, nitrobenzene, dimethyl sulfoxide, and N,N-dimethylformamide.

The aforementioned hetero-coupling reaction can be carried out in the presence of a metal catalyst and a base at a temperature in the range of 100-200° C. for a period in the range of 1-100 hours. Examples of the metal catalyst include a palladium complex that is formed from a palladium source such as palladium acetate and bis(benzylideneacetone)palladium and a ligand such as tri-tert-butylphosphine, copper powder, copper oxide, copper halide, and copper sulfate. Examples of the base include inorganic bases such as potassium carbonate, sodium carbonate, lithium hydroxide, sodium hydroxide, sodium tert-butoxide, and potassium tert-butoxide and organic bases such as pyridine, picoline, and triethylamine.

Upon completion of any of the aforementioned reactions, water is added to the reaction mixture to separate an organic layer, and the organic layer is concentrated, washed with a low-boiling solvent such as ethyl acetate, and dried under reduced pressure to give the compound of this invention. The compound is preferably purified further by sublimation when it is used as an organic EL material.

Concrete examples of the compounds of this invention represented by the aforementioned general formulas (1) and (2) are shown below, but this invention is not limited to these compounds.
TABLE 1
1
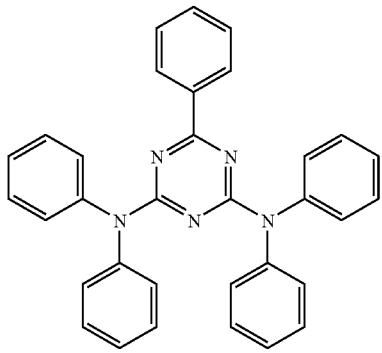
2
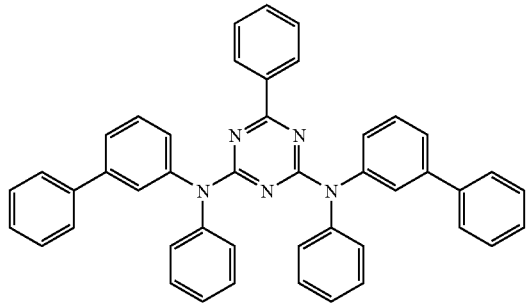
3
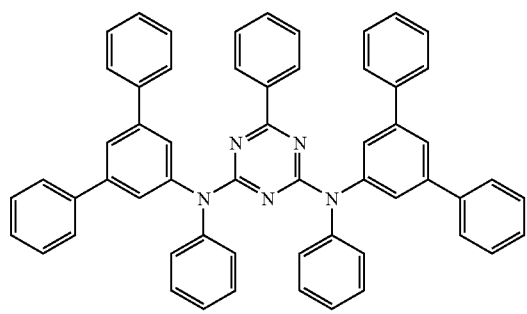
4
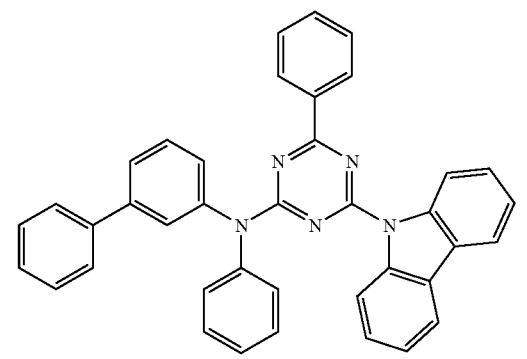
TABLE 1-continued
5
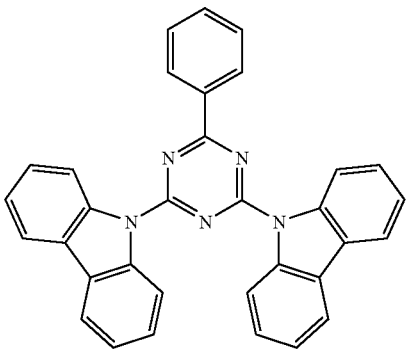
6
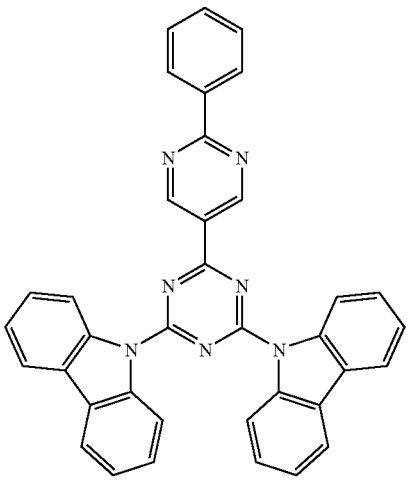
7
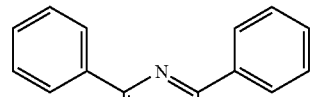
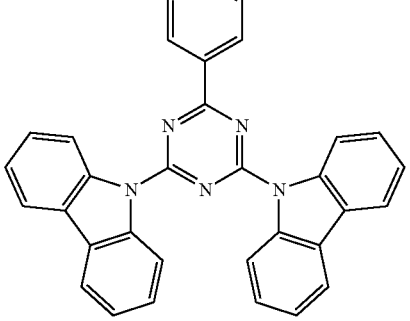

TABLE 1-continued
8
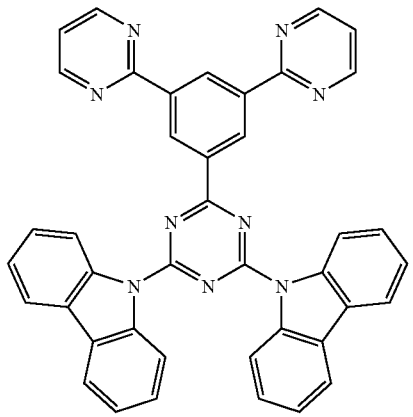
TABLE 2
9
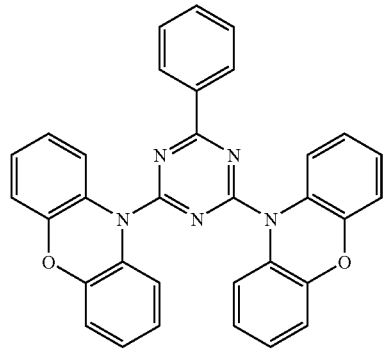
10
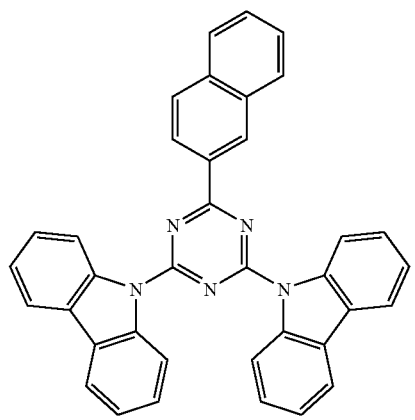
11
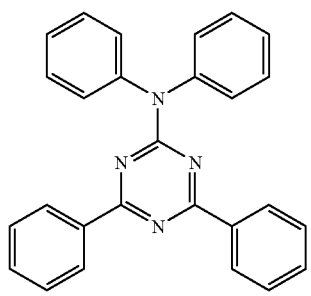
TABLE 2-continued
12
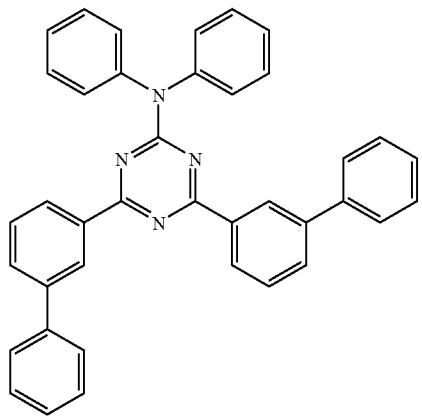
13
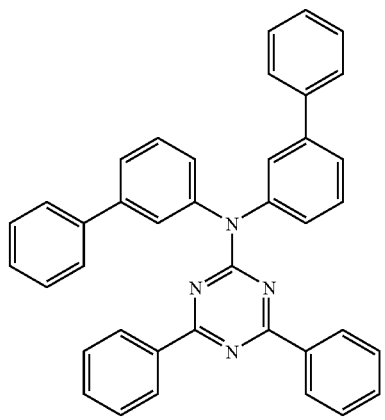
14
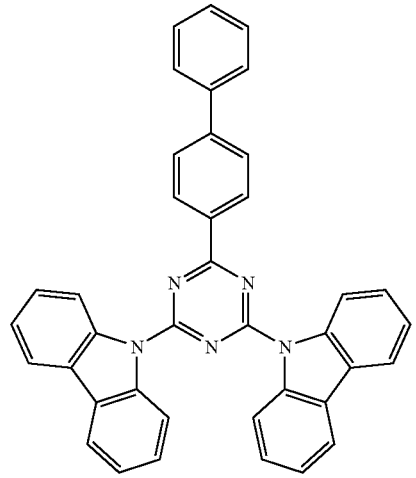

TABLE 2-continued
15
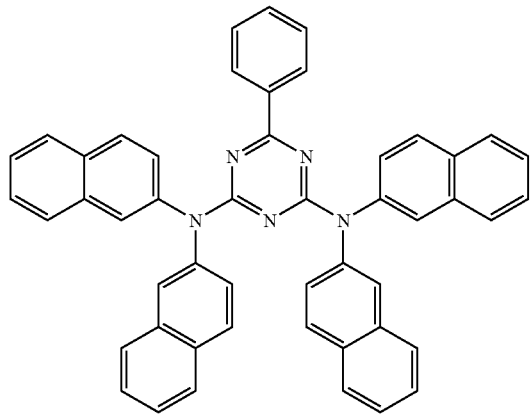
16
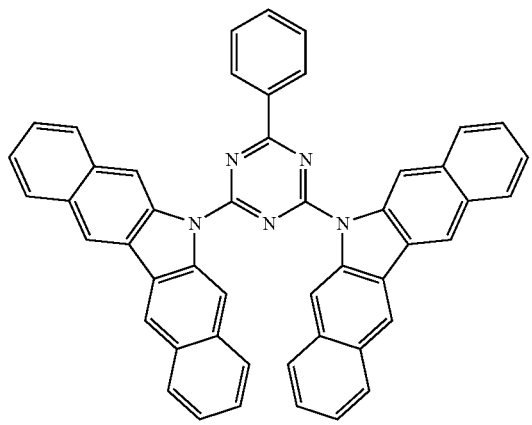
TABLE 3
17
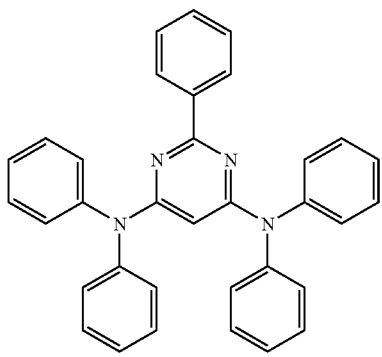
18
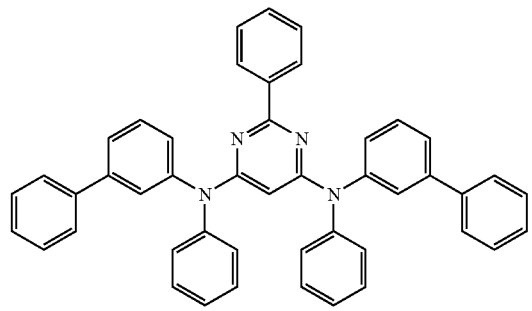
TABLE 3-continued
19
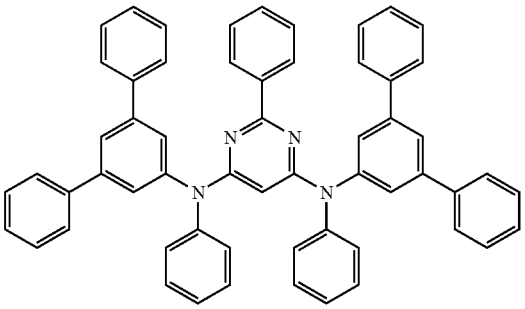
20
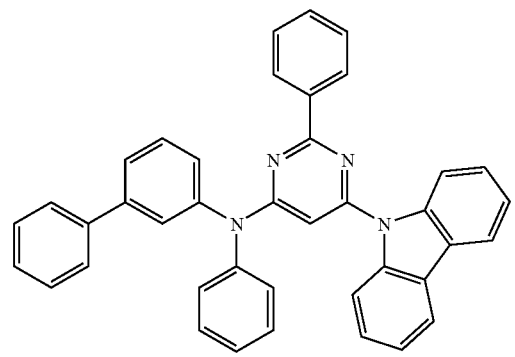
21
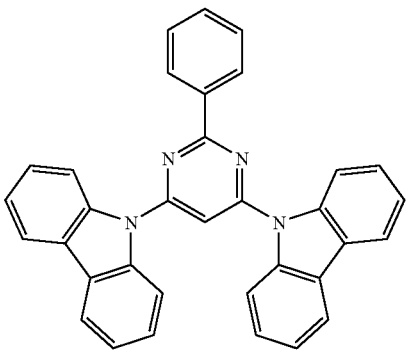
22
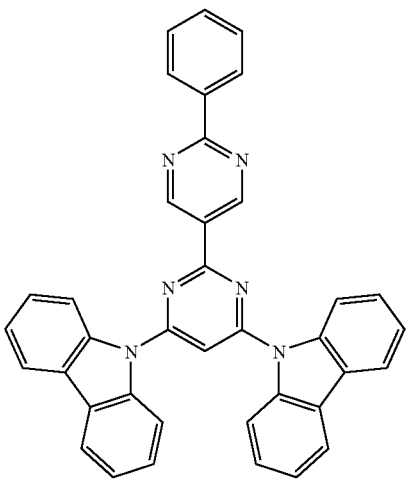

TABLE 3-continued
23
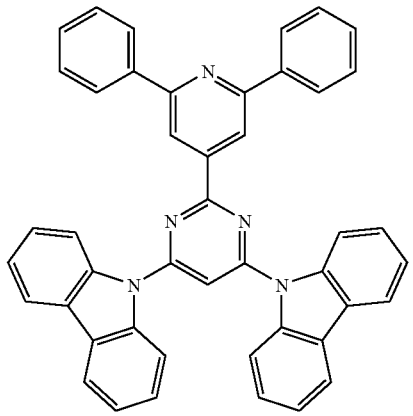
24
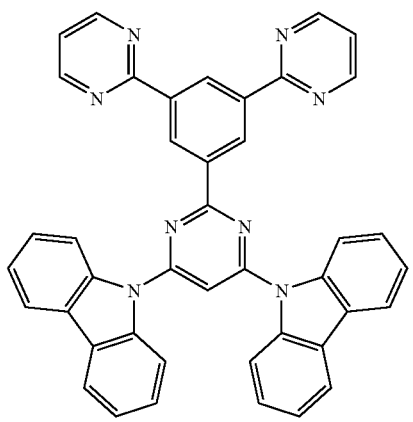
TABLE 4
25
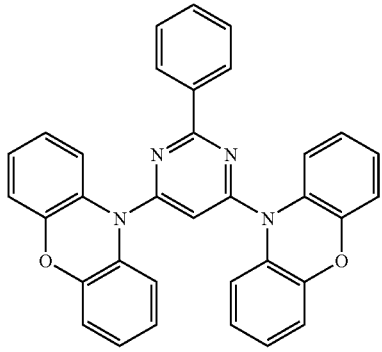
TABLE 4-continued
26
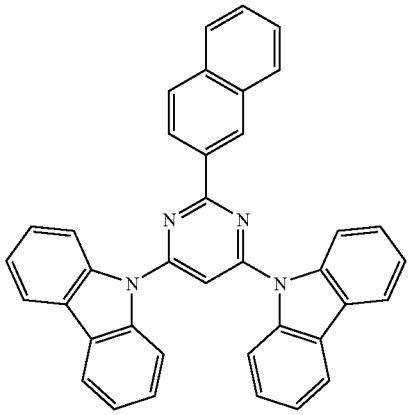
27
28
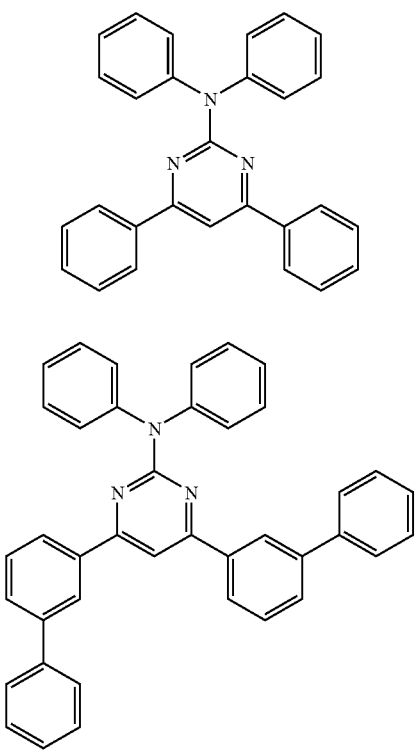
29
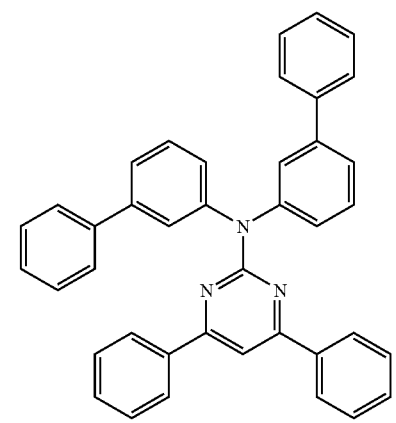

TABLE 4-continued
30
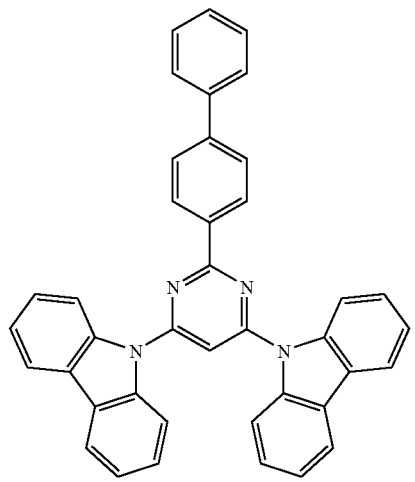
31
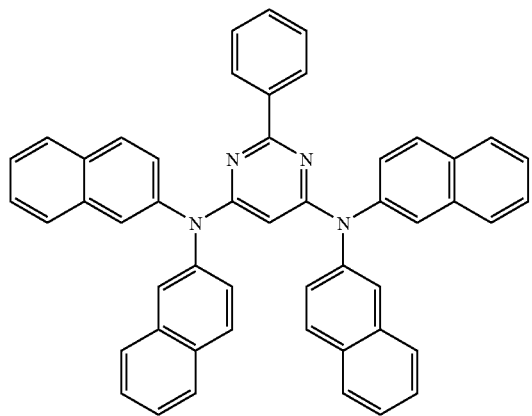
32
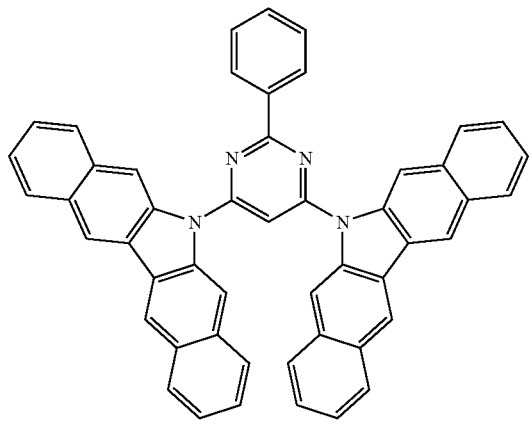
TABLE 5
33
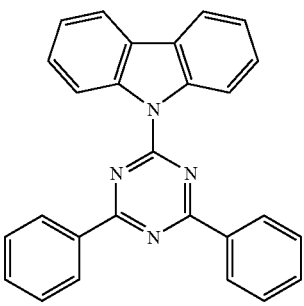
34
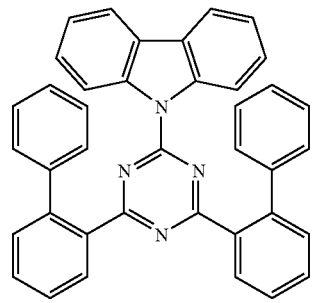
35
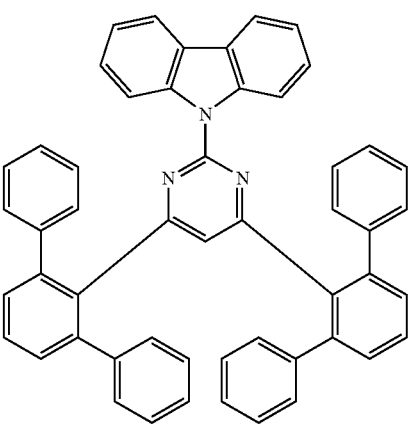
36
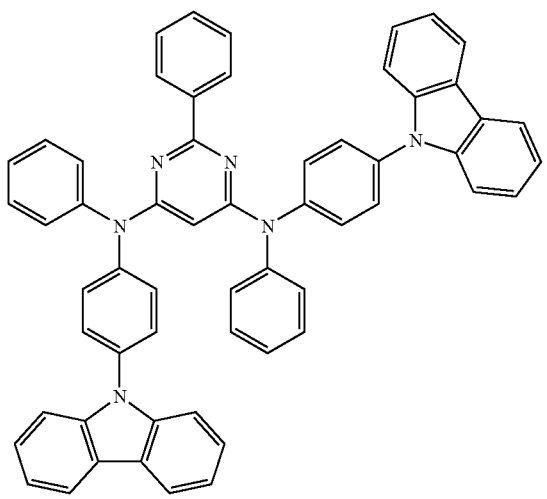

TABLE 5-continued
37
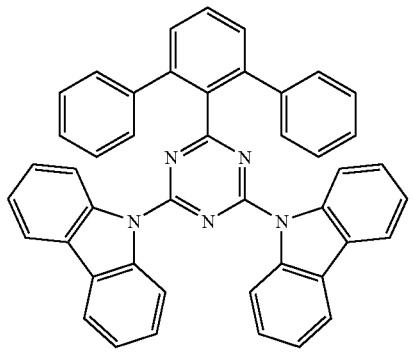
38
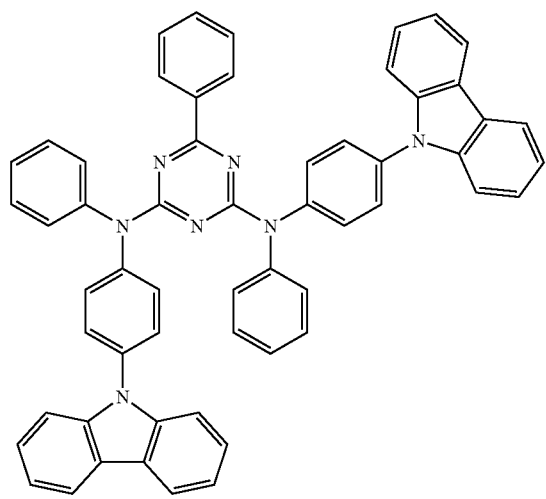
39
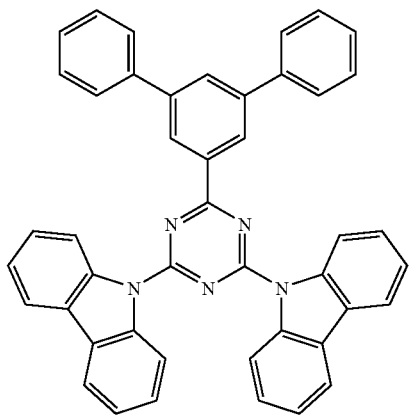
TABLE 5-continued
40
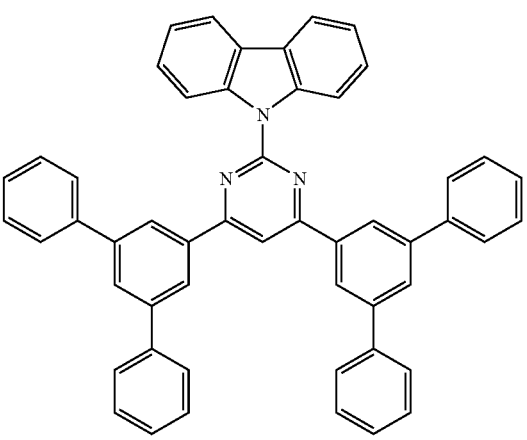
TABLE 6
41
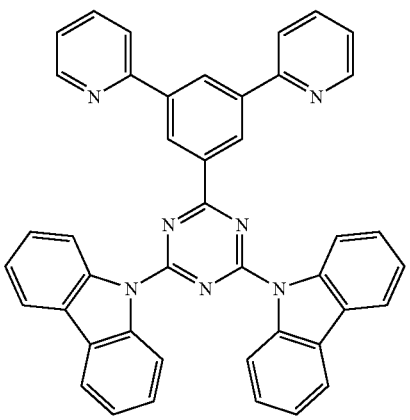
42
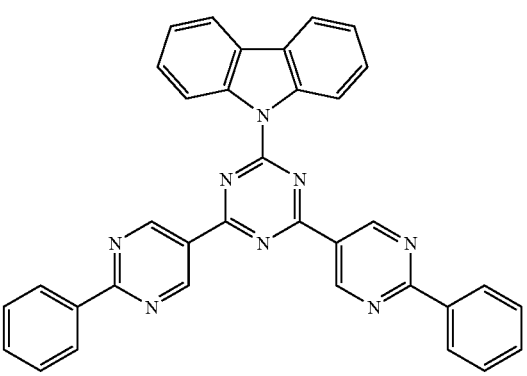

TABLE 6-continued
43
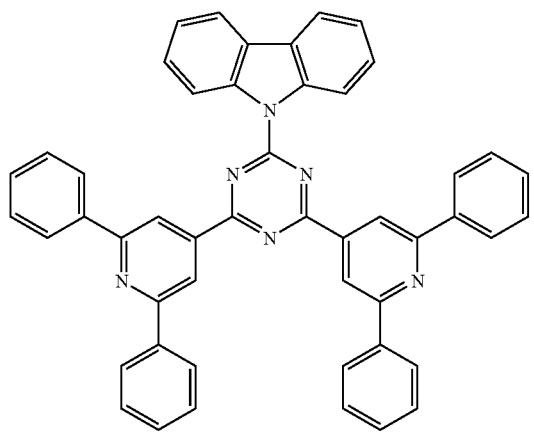
44
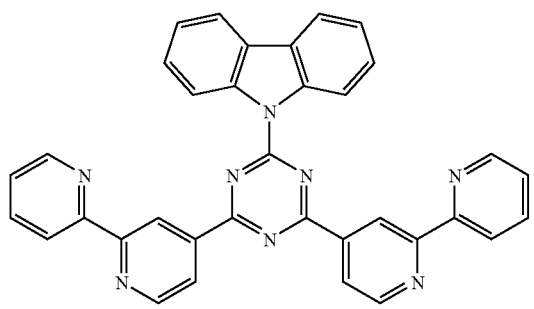
45
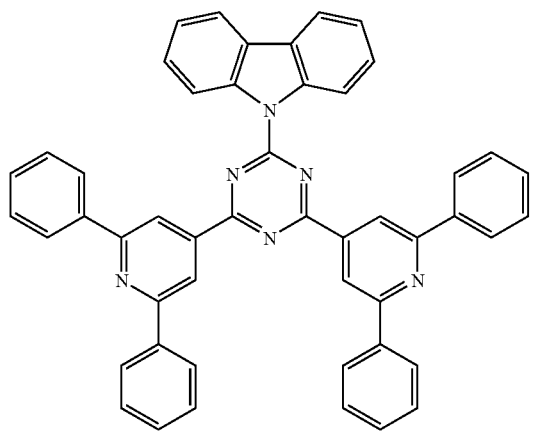
46
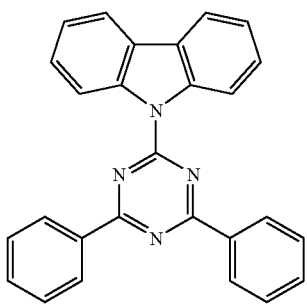
TABLE 6-continued
47
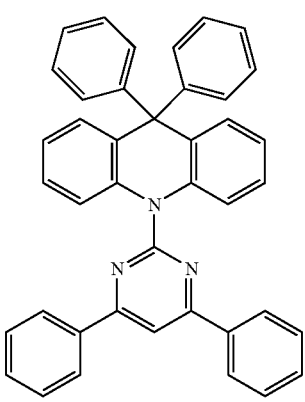
48
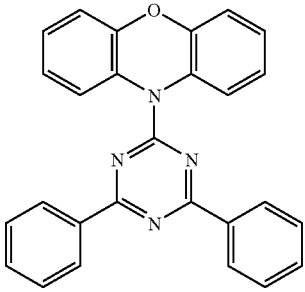
TABLE 7
49
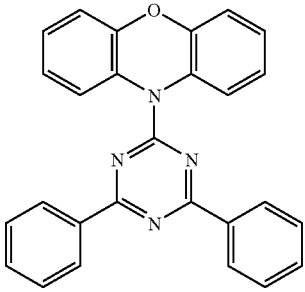
50
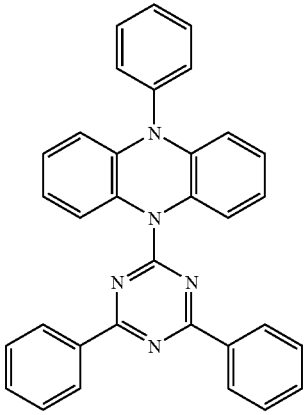

TABLE 7-continued

51 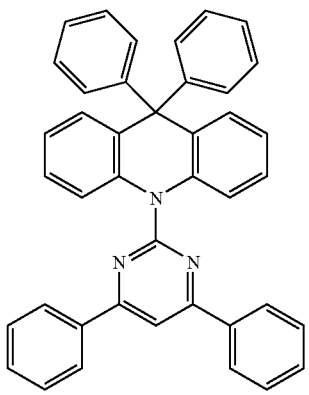

52 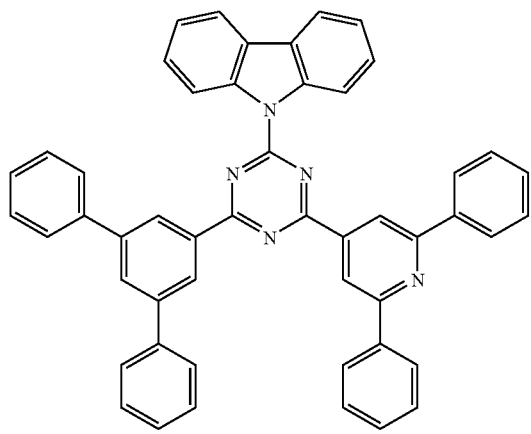

53 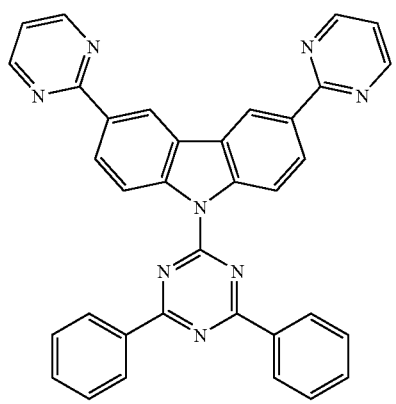

54 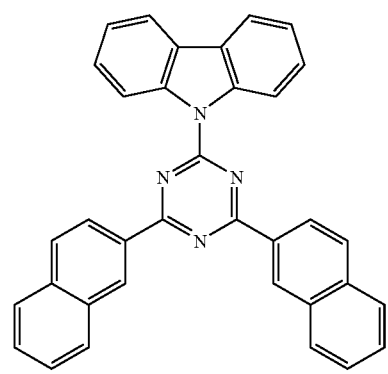

55 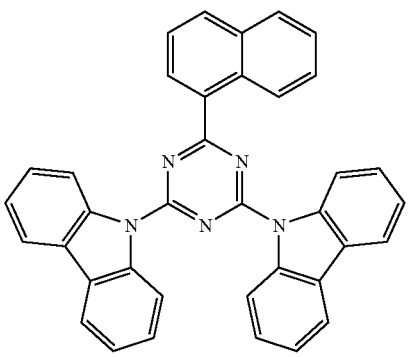

56

A compound for an organic electroluminescent device prepared according to this invention provides an excellent organic electroluminescent device when incorporated in organic layers of the organic EL device. Advantageously, the compound is incorporated in at least one organic layer selected from a light-emitting layer, a hole-transporting layer, an electron-transporting layer, and a hole-blocking layer. More preferably, the compound is incorporated as a host material of the light-emitting layer containing a phosphorescent dopant.

Phosphorescent dopants to be used in the light-emitting layer are preferably organic metal complexes containing at least one metal selected from ruthenium, rhodium, palladium, silver, rhenium, osmium, iridium, platinum, and gold. Such organic metal complexes are known in the aforementioned patent documents and elsewhere and a suitable complex can be selected from them and used in this invention.

Preferable phosphorescent dopants include complexes having a noble metal element such as Ir in the center, typically Ir(ppy)3, complexes such as Ir(bt)2·acac3, and complexes such as PtOEt3. Examples of these complexes are shown below, but are not limited thereto.

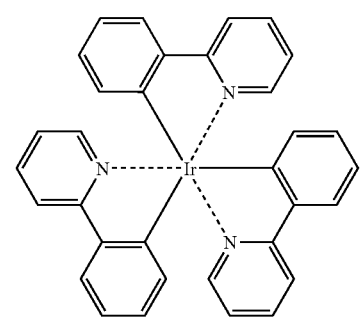
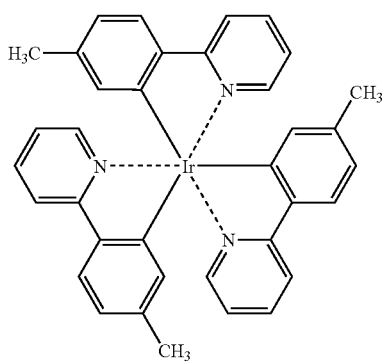
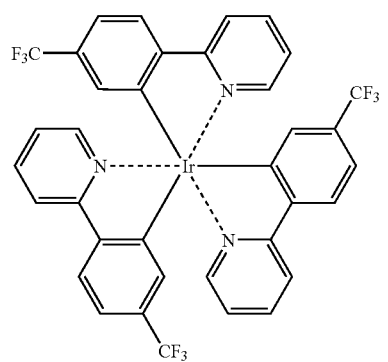
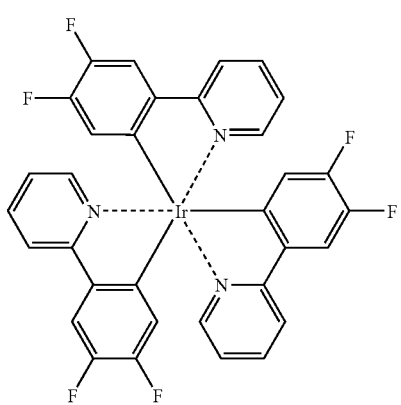
-continued
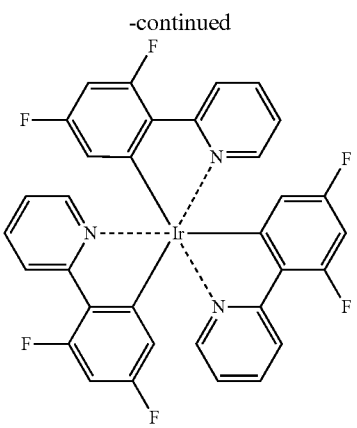
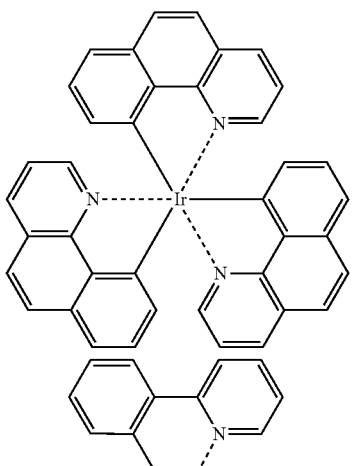
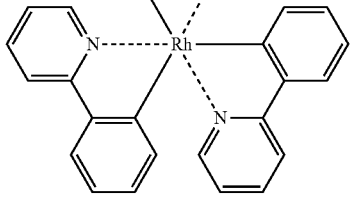
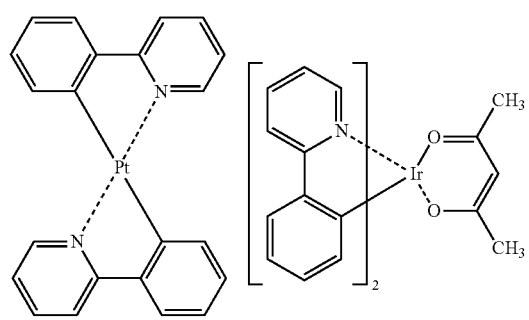
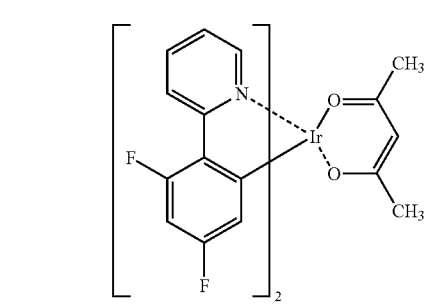

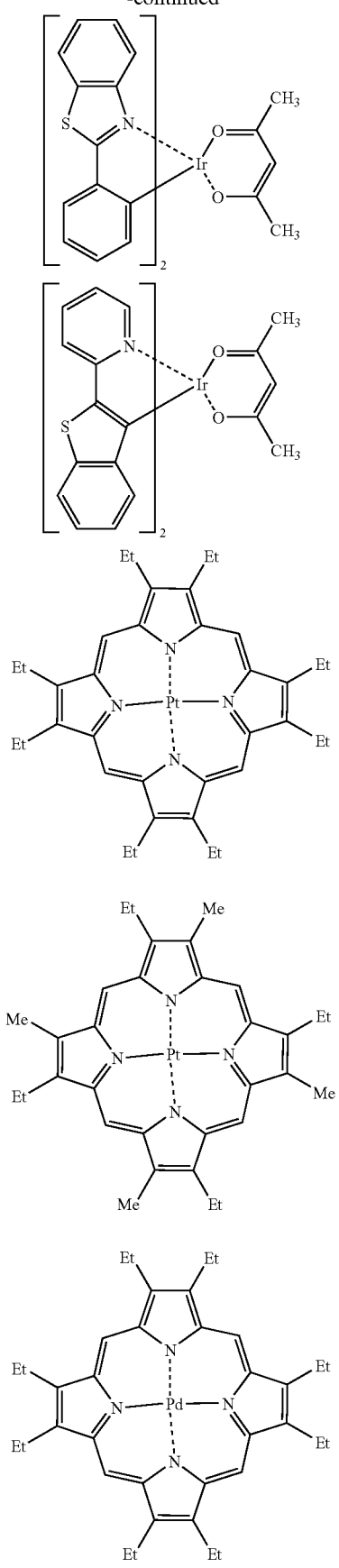
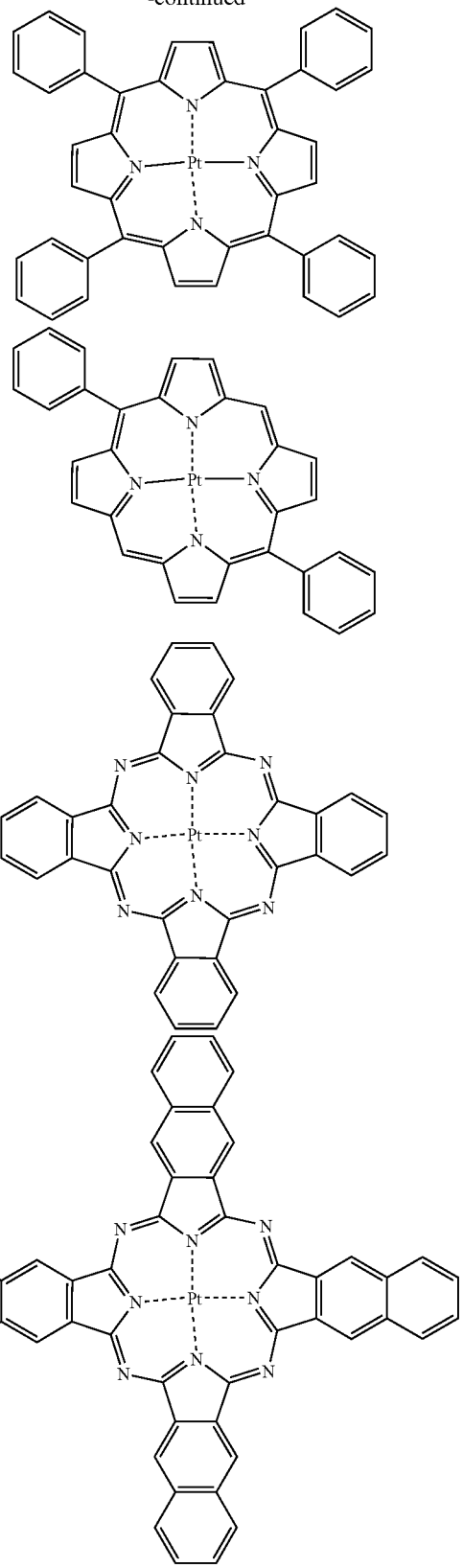
The content of the aforementioned phosphorescent dopant in the light-emitting layer is preferably in the range of 5-10 wt %.

An organic EL device using a compound of this invention will be explained next.

The organic EL device of this invention comprises at least one light-emitting layer disposed between an anode and a cathode piled one upon another on a substrate.

The structure of the organic EL device of this invention will be explained with reference to the drawing, but it will not be limited to the one shown in the drawing.

FIG. 1 schematically shows the structure of an example of an organic EL device generally used in this invention and the numbers in FIG. 1 respectively designate the following; 1 substrate, 2 anode, 3 hole-injecting layer, 4 hole-transporting layer, 5 light-emitting layer, 6 electron-transporting layer, and 7 cathode. The organic EL device of this invention comprises a substrate, an anode, a light-emitting layer, and a cathode as essential layers; in addition to the essential layers, the device preferably has a hole-injecting/transporting layer and an electron-injecting/transporting layer and, further, has a hole-blocking layer disposed between the light-emitting layer and the electron-injecting/transporting layer. The term hole-injecting/transporting layer means a hole-injecting layer and/or a hole-transporting layer and the term electron-injecting/transporting layer means an electron-injecting layer and/or an electron-transporting layer.

It is possible to fabricate a device with a structure that is the reverse of the one shown in FIG. 1 by piling the cathode 7, the electron-transporting layer 6, the light-emitting layer 5, the hole-transporting layer 4, and the anode 2 one upon another in this order on the substrate 1 and, as described earlier, it is possible to dispose the organic EL device of this invention between two substrates at least one of which is highly transparent. In this case of the reverse structure, a layer or layers may be added or omitted as needed.

The organic EL device of this invention is applicable to a single device, a device with its structure arranged in array, or a device in which the anode and the cathode are arranged in X-Y matrix. The organic EL device of this invention produces remarkable improvements in luminous efficiency and driving stability over the conventional devices utilizing emission of light from the excited singlet state by incorporating a compound of specific skeleton and a phosphorescent dopant in its light-emitting layer and the device can perform excellently when applied to full-color or multicolor panels.

EXAMPLES

This invention will be described in more detail below with reference to the examples; however, it will not be limited to these examples and it can be reduced to practice in various modes unless such practice exceeds the substance of this invention.

Compounds 2, 3, 5, 33, 34, 36, 37, and 38 were synthesized respectively by the routes shown below. The compound numbers correspond to those in Tables 1 to 7.

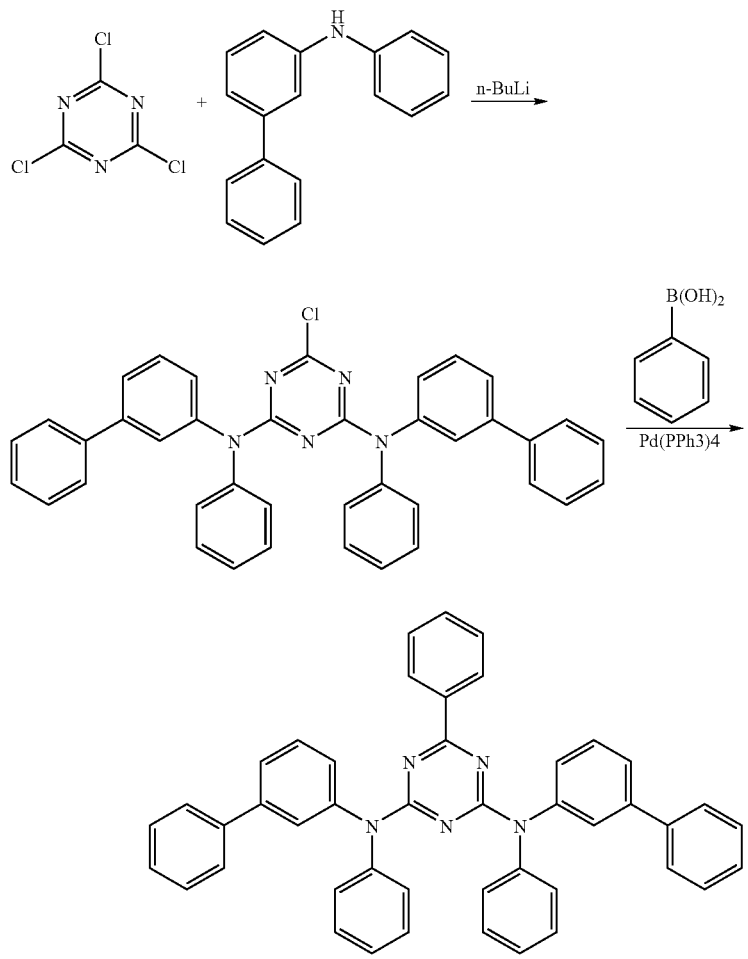

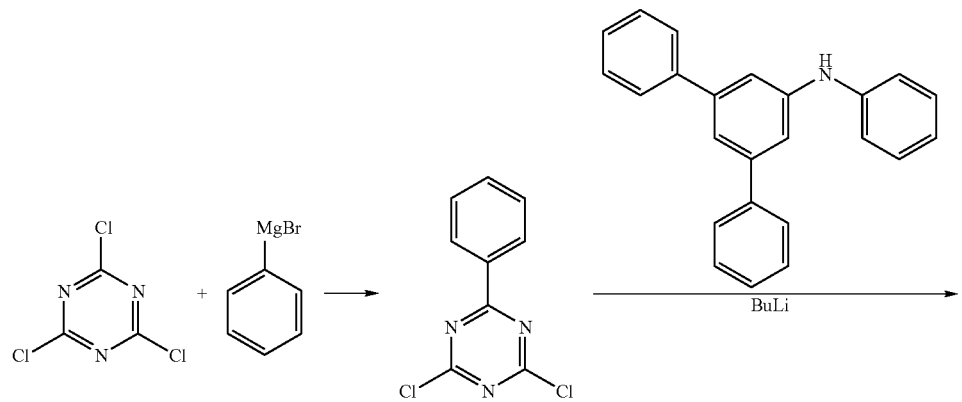
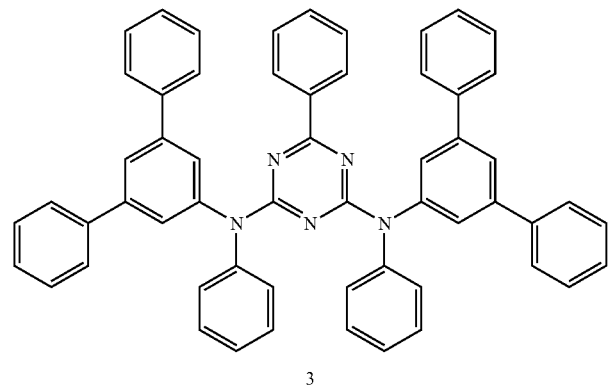
3
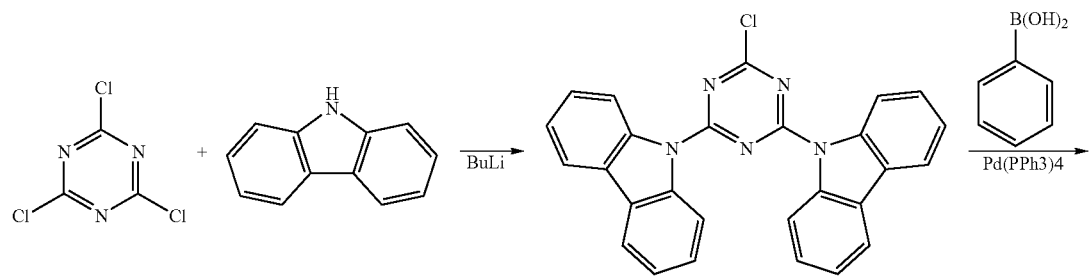
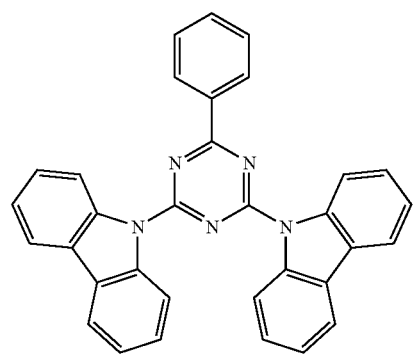
5

-continued
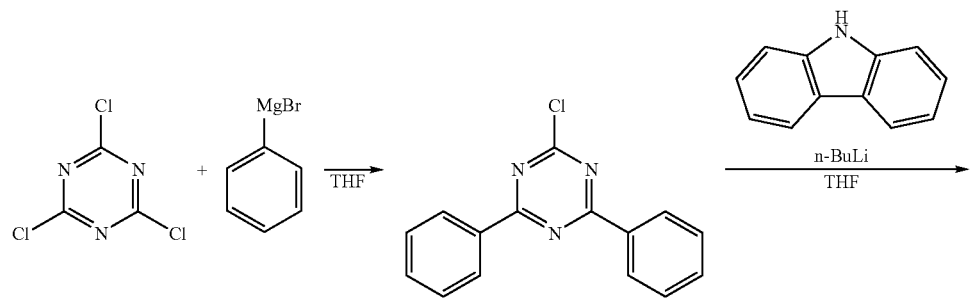
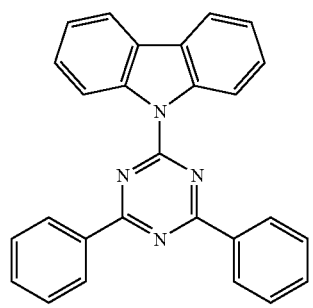
33
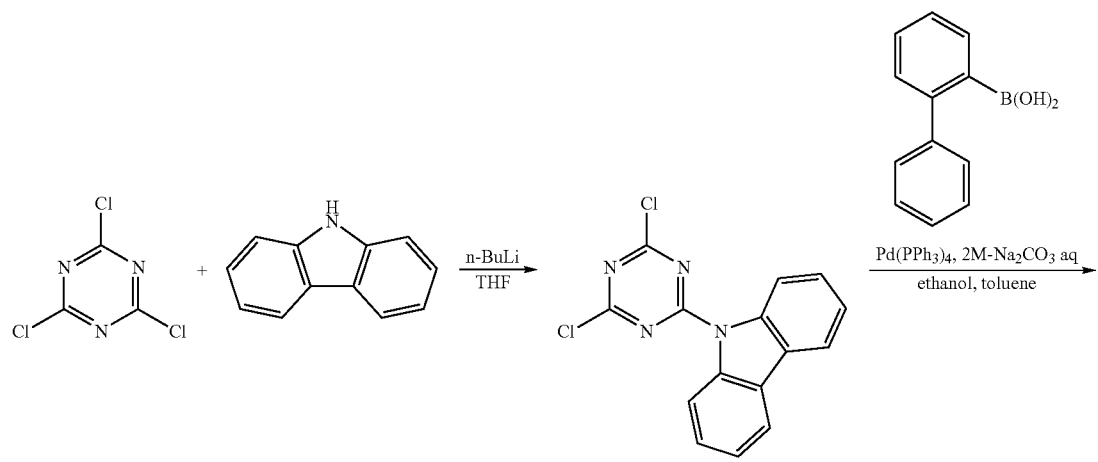
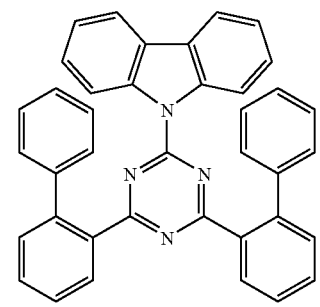
34

-continued
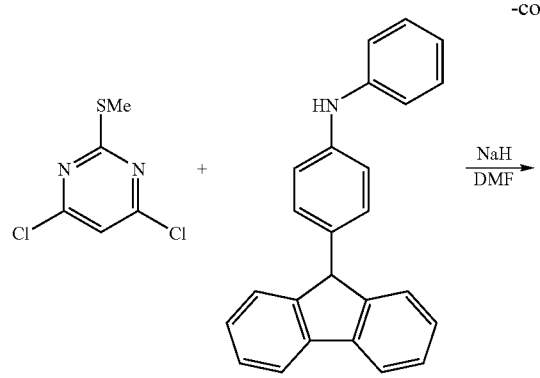
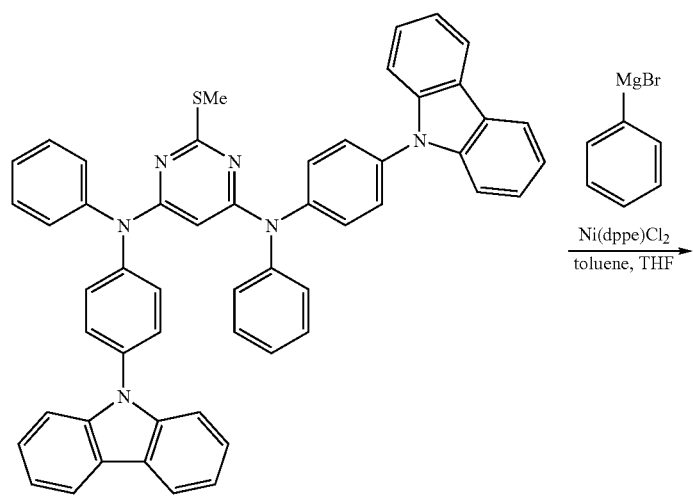
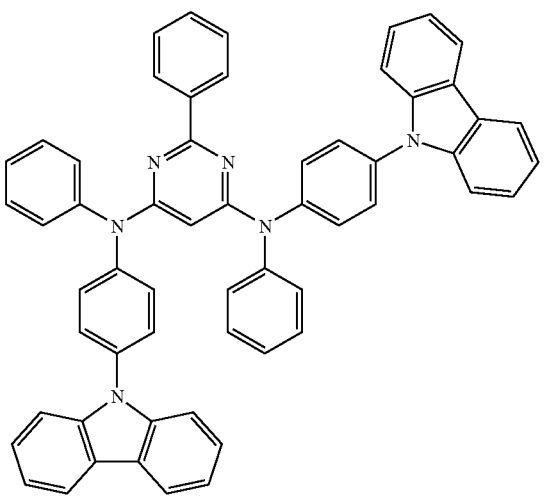
36
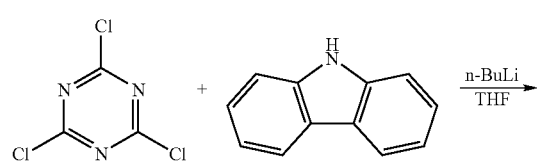

-continued
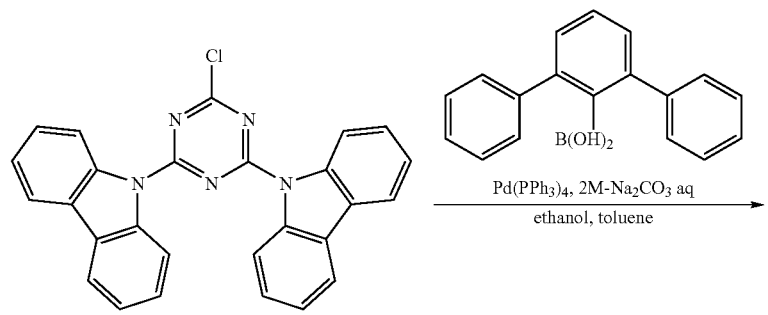
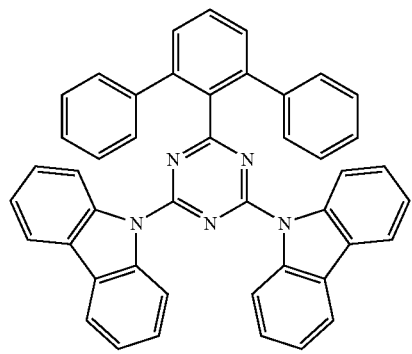
37
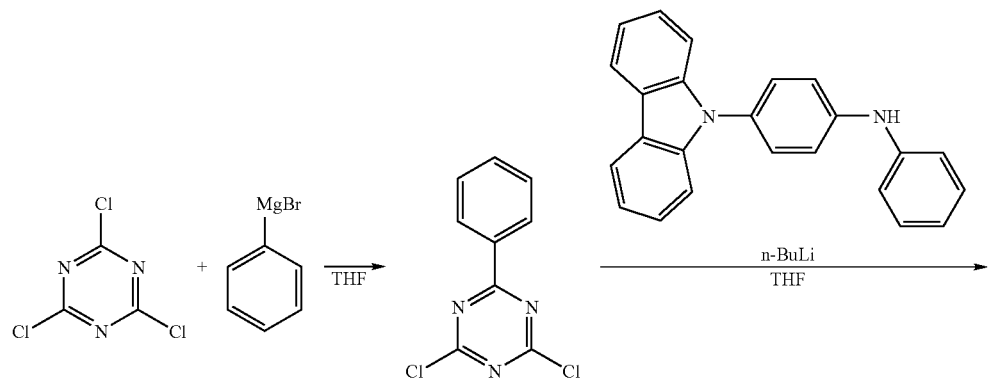
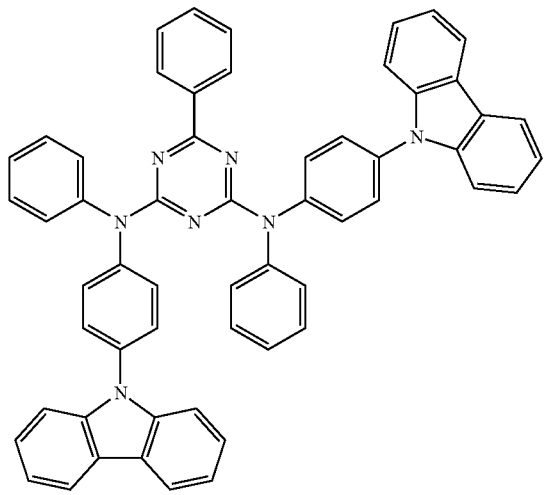
38

Example 1

Synthesis of Compound 2

In a 500-ml three-necked flask was placed 25.0 g (0.102 mole) of N-(3-biphenylyl)phenylamine, 200 ml of THF was added, and the mixture was stirred under flow of nitrogen. The resulting solution was cooled to 0° C. in an ice bath and a solution of 0.122 mole of n-butyllithium in 77 ml of n-hexane was added dropwise over 15 minutes. The mixture was then stirred at room temperature for 30 minutes to prepare a lithium reagent. Then, 8.9 g (0.048 mole) of cyanuric chloride and 200 ml of THF were placed in a 1,000-ml three-necked flask and the mixture was stirred under flow of nitrogen. To this was added dropwise the lithium reagent prepared earlier over 20 minutes. After the dropwise addition, the mixture was stirred at 55° C. for 1.5 hours. The mixture was cooled to room temperature, 300 ml of water and 100 ml of toluene were added, and the mixture was stirred and separated into an organic layer and an aqueous layer. The organic layer was washed three times with 100 ml of water and then dehydrated over magnesium sulfate, the magnesium sulfate was filtered out, and the solvent was distilled off under reduced pressure. The residue was then purified by column chromatography to give 21.5 g (0.036 mole, 74.4% yield) of a white solid.

Then, 19.0 g (0.032 mole) of the aforementioned white solid, 3.5 g (0.028 mole) of phenylboronic acid, 0.44 g (0.0004 mole) of tetrakis(triphenylphosphine)palladium(0), 60 ml of ethanol, and 180 ml of toluene were placed in a 500-ml three-necked flask and stirred. To this was added 60 ml of an aqueous solution containing 15.8 g of sodium carbonate and the mixture was stirred at 75° C. for 1.5 hours. The mixture was cooled to room temperature, 150 ml of toluene was added, and the mixture was stirred and separated into an organic layer and an aqueous layer. The organic layer was washed three times with 100 ml of water and then dehydrated over magnesium sulfate, the magnesium sulfate was filtered out, and the solvent was distilled off under reduced pressure. The residue was then purified by column chromatography to give 9.5 g of a white solid. The white solid was further purified by crystallization from dichloromethane and ethanol to give 7.7 g of Compound 2.

FD-MS, m/z 643 [M]$^+$; melting point, 198° C.

Example 2

Synthesis of Compound 3

In a 1,000-ml three-necked flask were placed 20.9 g (0.113 mole) of cyanuric chloride and 200 ml of THF and stirred under flow of nitrogen. To this was added dropwise a solution of 0.108 mole of phenylmagnesium bromide in 100 ml of THF over 20 minutes and the mixture was stirred at room temperature for 2.5 hours. To the mixture were added 200 ml of water and 100 ml of toluene and the mixture was stirred and separated into an organic layer and an aqueous layer. The organic layer was washed three times with 100 ml of water and then dehydrated over magnesium sulfate, the magnesium sulfate was filtered out, and the solvent was distilled off under reduced pressure. The residue was then reslurried in methanol to give 13.9 g (0.061 mole, 54.4% yield) of a light yellow solid.

Then, 15.5 g (0.048 mole) of N-(3,5-diphenylphenyl)phenylamine and 150 ml of THF were placed in a 500-ml three-necked flask and stirred under flow of nitrogen. The resulting solution was cooled to 0° C. in an ice bath and a solution of 0.053 mole of n-butyllithium in 34 ml of n-hexane was added dropwise over 15 minutes. The mixture was then returned to room temperature and stirred for 30 minutes to prepare a lithium reagent. Then, 5.0 g (0.022 mole) of the aforementioned light yellow solid and 150 ml of THF were placed in a 1,000-ml three-necked flask and stirred under flow of nitrogen. To this was added dropwise the lithium reagent prepared earlier over 20 minutes. After the dropwise addition, the mixture was heated to 55° C. and stirred for 3.5 hours. The mixture was cooled to room temperature, 200 ml of water and 150 ml of toluene were added, and the mixture was stirred and separated into an organic layer and an aqueous layer. The organic layer was washed three times with 100 ml of water and then dehydrated over magnesium sulfate, the magnesium sulfate was filtered out, the solvent was distilled under reduced pressure, and a yellow solid weighing 20.7 g was obtained. The solid was crystallized from THF and methanol to give 8.8 g (0.011 mole, 50.0% yield) of Compound 3.

FD-MS, m/z 795 [M]$^+$; melting point, 252° C.

Example 3

Synthesis of Compound 5

In a 500-ml three-necked flask were placed 20.0 g (0.120 mole) of carbazole and 120 ml of THF and stirred under flow of nitrogen. The resulting solution was cooled to 0° C. in an ice bath and a solution of 0.127 mole of n-butyllithium in 80 ml of n-hexane was added dropwise over 15 minutes. The mixture was then stirred at room temperature for 20 minutes to prepare a lithium reagent. Then, 11.0 g (0.060 mole) of cyanuric chloride and 120 ml of THF were placed in a 500-ml three-necked flask and stirred under flow of nitrogen. To this was added dropwise the lithium reagent prepared earlier over 15 minutes. After the dropwise addition, the mixture was heated to 55° C. and stirred for 1 hour. The mixture was cooled to room temperature, 100 ml of water was added to precipitate a solid, and the solid was collected by filtration, rinsed with a mixture of 100 ml of water and 100 ml of THF, rinsed further with 50 ml of methanol, and dried under reduced pressure to give 20.2 g (0.045 mole, 75.5% yield) of a yellow powder.

In a 500-ml three-necked flask were placed 10.0 g (0.022 mole) of the aforementioned white powder, 3.5 g (0.028 mole) of phenylboronic acid, 0.44 g (0.0004 mole) of tetrakis (triphenylphosphine)palladium(0), 60 ml of ethanol, and 180 ml of toluene and stirred. To this was added 60 ml of an aqueous solution containing 11.4 g of sodium carbonate and the mixture was stirred at 75° C. for 1.5 hours. The mixture was cooled to room temperature, 100 ml of water was added, the mixture was stirred, and a precipitate was collected by filtration. The precipitate was a black solid weighing 8.9 g. To the black solid were added 120 ml of THF and 120 ml of toluene and the solid was reslurried with application of heat to give 6.5 g of a gray solid. To the gray solid were added 650 g of THF and 0.7 g of activated carbon and the mixture was stirred at room temperature for 1 hour. The mixture was then filtered through Celite and the filtrate was concentrated under reduced pressure to give 6.0 g of a white solid. The white solid was further purified by crystallization from THF and methanol to give 2.5 g of Compound 5.

FD-MS, m/z 487 [M]$^+$; melting point, 274° C.

Example 4

Synthesis of Compound 33

In a 1,000-ml three-necked flask were placed 25.0 g (0.135 mole) of cyanuric chloride and 110 ml of THF and stirred under flow of nitrogen. To this was added dropwise a solution of 0.371 mole of phenylmagnesiium bromide in 344 ml of THF over 20 minutes and then the mixture was stirred at room temperature for 2.5 hours. To the mixture were added 200 ml of water and 150 ml of toluene and the mixture was stirred and separated into an organic layer and an aqueous layer. The organic layer was washed three times with 100 ml of water and then dehydrated over magnesium sulfate, the magnesium sulfate was filtered out, the solvent was distilled off under reduced pressure, and a yellow solid weighing 30.5 g was obtained. To the yellow solid was added 145 g of methanol and the solid was reslurried with application of heat to give 21.0 g (0.078 mole, 58.1% yield) of a light yellow solid.

Then, 18.8 g (0.112 mole) of carbazole and 125 ml of THF were placed in a 1,000-ml three-necked flask and stirred under flow of nitrogen. The resulting solution was cooled to 0° C. in an ice bath and a solution of 0.135 mole of n-butyllithium in 85 ml of n-hexane was added dropwise over 15 minutes. The mixture was then returned to room temperature and stirred for 20 minutes to prepare a lithium reagent. Then, 20.0 g (0.075 mole) of the aforementioned light yellow solid and 120 ml of THF were placed in a 500-ml three-necked flask and stirred under flow of nitrogen. To this was added dropwise the lithium reagent prepared earlier. After the dropwise addition, the mixture was heated under reflux with stirring for 23 hours. The mixture was cooled to room temperature, 200 ml of water and 65 ml of methanol were added, the mixture was stirred, a precipitate was collected by filtration, and a yellow solid weighing 18.3 g was obtained. The yellow solid was purified by crystallization from chloroform and methanol to give 6.6 g (0.017 mole, 22.1% yield) of Compound 33.

APCI-MS, m/z 399 [M+H]$^+$; melting point, 286° C.

Example 5

Synthesis of Compound 34

In a 500-ml three-necked flask were placed 19.0 g (0.114 mole) of carbazole and 120 ml of THF and stirred under flow of nitrogen. The resulting solution was cooled to 0° C. in an ice bath and a solution of 0.114 mole of n-butyllithium in 72 ml of n-hexane was added dropwise over 30 minutes. The mixture was then stirred at room temperature for 30 minutes to prepare a lithium reagent. Then, 20.0 g (0.108 mole) of cyanuric chloride and 120 ml of THF were placed in a 1,000-ml three-necked flask and stirred under flow of nitrogen. To this was added dropwise the lithium reagent prepared earlier over 30 minutes. After the dropwise addition, the mixture was stirred at room temperature for 1.0 hour. Then, 240 ml of water was added to the mixture to precipitate a white solid. The white solid was collected by filtration and purified by recrystallization from methanol and toluene to give 19.0 g (0.0603 mole, 95.4% yield) of a white solid.

Then, 14.0 g (0.0444 mole) of the aforementioned white powder, 21.1 g (0.107 mole) of 2-biphenylboronic acid, 2.8 g (0.0018 mole) of tetrakis(triphenylphosphine)palladium(0), 140 ml of ethanol, and 420 ml of toluene were placed in a 2,000-ml three-necked flask and stirred. To this was added 168 ml of an aqueous solution containing 35.0 g of sodium carbonate and the mixture was stirred at 90° C. overnight. The mixture was cooled to room temperature, 200 ml of water and 200 ml of toluene were added, and the mixture was stirred and separated into an organic layer and an aqueous layer. The organic layer was washed three times with 200 ml of water and then dehydrated over magnesium sulfate, the magnesium sulfate was filtered out, and the solvent was distilled off under reduced pressure. The residue was then recrystallized from chloroform and toluene to give 7.40 g (0.0134 mole, 30.0% yield) of Compound 34 as a white powder.

FD-MS, m/z 551 [M+H]$^+$; melting point, 227° C.

Example 7

Synthesis of Compound 36

In a 500-ml three-necked flask were placed 2.69 g (0.066 mole) of sodium hydride and 50 ml of DMF and stirred under flow of nitrogen. To this was added dropwise a solution of 20.0 g (0.060 mole) of N-(4-carbazolylphenyl)phenylamine in 100 ml of DMF and the mixture was stirred at room temperature for 30 minutes. Then, a solution of 4.86 g (0.025 mole) of 4,6-dichloro-2-methylthiopyrimidine in 50 ml of DMF was added dropwise. After the dropwise addition, the mixture was stirred at 50° C. for 2.5 hours. The mixture was cooled to room temperature, 200 ml of water was added, the mixture was stirred, a precipitate was collected by filtration, and a red solid weighing 18.8 g was obtained. To the red solid was added 200 g of toluene and the solid was purified by reslurrying with application of heat to give 13.2 g (0.017 mole, 66.8% yield) of a white solid.

Then, 12.0 g (0.015 mole) of the aforementioned white solid, 0.16 g (0.0003 mole) of [1,2-bis(diphenylphosphino)ethane]dichloronickel(II), and 100 ml of toluene were placed in a 500-ml three-necked flask and stirred for 10 minutes under flow of nitrogen. To this was added a solution of 0.023 mole of phenylmagnesium bromide in 21.1 ml of THF and the mixture was stirred at 60° C. for 1 hour. Then, the mixture was returned to room temperature, 100 ml of 1 M hydrochloric acid was added, the mixture was stirred, a precipitate was collected by filtration, and a red solid weighing 9.6 g was obtained. The red solid was recrystallized from THF to give 3.7 g (0.0045 mole, 29.7% yield) of Compound 36.

APCI-MS, m/z 821 [M+H]$^+$; melting point, 293° C.

Example 8

Synthesis of Compound 37

In a 500-ml three-necked flask were placed 20.0 g (0.120 mole) of carbazole and 120 ml of THF and stirred under flow of nitrogen. The resulting solution was cooled to 0° C. in an ice bath and a solution of 0.127 mole of n-butyllithium in 80 ml of n-hexane was added dropwise over 30 minutes. The mixture was then returned to room temperature and stirred for 20 minutes to prepare a lithium reagent. Then, 11.0 g (0.0599 mole) of cyanuric chloride and 120 ml of THF were placed in a 1,000-ml three-necked flask and stirred under flow of nitrogen. To this was added dropwise the lithium reagent prepared earlier over 30 minutes. After the dropwise addition, the mixture was stirred at 60° C. for 1.5 hours. The mixture was cooled to room temperature and 200 ml of water was added to precipitate a white solid. The white precipitate was collected by filtration and purified by reslurrying in methanol with application of heat to give 16.0 g (0.0359 mole, 59.9% yield) of a white solid.

Then, 10.0 g (0.0224 mole) of the aforementioned white solid, 7.38 g (0.0269 mole) of m-terphenyl-2'-boronic acid, 1.7 g (0.0011 mole) of tetrakis(triphenylphosphine)palladium(0), 100 ml of ethanol, and 400 ml of toluene were placed in a 2,000-ml three-necked flask and stirred. To this was added 40 ml of an aqueous solution containing 8.55 g of sodium carbonate and the mixture was stirred at 90° C. overnight. The mixture was cooled to room temperature, 200 ml of water and 500 ml of toluene were added, and the mixture was stirred and separated into an organic layer and an aqueous layer. The organic layer was washed three times with 200 ml of water and then dehydrated over magnesium sulfate, the magnesium sulfate was filtered out, and the solvent was distilled off under reduced pressure. The residue was then purified by reslurrying in THF and toluene with application of heat to give 3.10 g (0.00485 mole, 21.7% yield) of Compound 37 as a white powder.

FD-MS, m/z 640 [M+H]$^+$; melting point, 307° C.

Example 9

Synthesis of Compound 38

In a 1,000-ml three-necked flask were placed 20.9 g (0.113 mole) of cyanuric chloride and 200 ml of THF and stirred under flow of nitrogen. To this was added dropwise a solution of 0.108 mole of phenylmagnesium bromide in 100 ml of THF over 20 minutes and then the mixture was stirred at room temperature for 2.5 hours. To the mixture were added 200 ml of water and 100 ml of toluene and the mixture was then stirred and separated into an organic layer and an aqueous layer. The organic layer was washed three times with 100 ml of water and then dehydrated over magnesium sulfate, the magnesium sulfate was filtered out, and the solvent was distilled off under reduced pressure. The residue was then purified by reslurrying in methanol to give 13.9 g (0.061 mole, 54.4% yield) of a light yellow solid.

Then, 15.0 g (0.041 mole) of N-(4-carbozolylphenyl)phenylamine and 150 ml of THF were placed in a 300-ml three-necked flask and stirred under flow of nitrogen. The resulting solution was cooled to 0° C. in an ice bath and a solution of 0.049 mole of n-butyllithium in 30 ml of n-hexane was added dropwise over 15 minutes. The mixture was then returned to room temperature and stirred for 30 minutes to prepare a lithium reagent. Then, 4.2 g (0.018 mole) of the aforementioned light yellow solid and 250 ml of THF were placed in a 1,000-ml three-necked flask and stirred under flow of nitrogen. To this was added dropwise the lithium reagent prepared earlier. After the dropwise addition, the mixture was heated under reflux with stirring for 4.5 hours. The mixture was cooled to room temperature, 200 ml of water was added, a precipitate was collected by filtration, and a light yellow solid weighing 14.4 g was obtained. The light yellow solid was purified by reslurrying in ethyl acetate to give 13.1 g of a white solid. The white solid was further purified by crystallization from dichloromethane and ethanol to give 10.0 g (0.012 mole, 66.7% yield) of Compound 38.

APCI-MS, m/z 822 [M+H]$^+$; melting point, 258° C.

Example 10

An organic EL device having the structure shown in FIG. 1 plus an electron-injecting layer was fabricated as follows. Applying the vacuum deposition process at a degree of vacuum of $4.0 \times 10^{-4}$ Pa, the constituent layers in thin films were piled one upon another on a glass substrate having a 150 nm-thick indium tin oxide (ITO) anode formed thereon. First, copper phthalocyanine (CuPC) was deposited on the ITO anode to a thickness of 25 nm as a hole-injecting layer. Then, NPB was deposited to a thickness of 40 nm as a hole-transporting layer. Next, a light-emitting layer was formed on the hole-transporting layer to a thickness of 40 nm by co-depositing Compound 2 as the main component of the light-emitting layer and Ir(ppy)3 as a guest material (phosphorescent dopant) from different evaporation sources. The concentration of Ir(ppy)3 was 7.0%. Then, Alq3 was deposited to a thickness of 20 nm as an electron-transporting layer. Further, lithium fluoride (LiF) was deposited on the electron-transporting layer to a thickness of 0.5 nm as an electron-injecting layer. Finally, aluminum (Al) as an electrode was deposited on the electron-injecting layer to a thickness of 170 nm to complete the fabrication of an organic EL device.

The organic EL device thus fabricated was connected to an outside power source and, upon application of direct current voltage, emission of light from the device with the characteristics shown in Table 8 was confirmed. The luminance, voltage, luminous efficiency, and luminance half life in Table 8 are measured at 10 mA/cm$^2$. The maximum wavelength of the spectrum of light emitted from the device is 517 nm and this proves that light is emitted from Ir(ppy)3.

Example 11

An organic EL device was fabricated as in Example 10 with the exception of using Compound 3 as the main component of the light-emitting layer.

Example 12

An organic EL device was fabricated as in Example 10 with the exception of using Compound 5 as the main component of the light-emitting layer.

Comparative Example 1

An organic EL device was fabricated as in Example 10 with the exception of using the following compound (Compound H-1) as the main component of the light-emitting layer.

The luminous characteristics of the organic EL devices are shown in Table 8.

TABLE 8

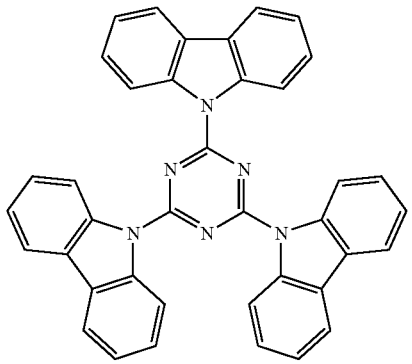

| | Compound | Luminance (cd/m$^2$) | Voltage (V) | Luminous efficiency (lm/W) | Luminance half life (h) |
|---|---|---|---|---|---|
| Example 10 | 2 | 4250 | 8.1 | 16.5 | 550 |
| Example 11 | 3 | 3900 | 7.9 | 15.5 | 1050 |
| Example 12 | 5 | 3300 | 7.5 | 13.8 | 1200 |
| Comparative example 1 | H-1 | 3200 | 8.2 | 12.3 | 55 |

Example 13

An organic EL device having the structure shown in FIG. 1 plus an electron-injecting layer disposed between a cathode and an electron-transporting layer was fabricated as follows.

Applying the vacuum deposition process at a degree of vacuum of 4.0×10$^{-4}$ Pa, the constituent layers in thin films were piled one upon another on a glass substrate having a 110 nm-thick indium tin oxide (ITO) anode formed thereon. First, copper phthalocyanine (CuPC) was deposited on the ITO anode to a thickness of 30 nm as a hole-injecting layer. Then, NPB was deposited to a thickness of 80 nm as a hole-transporting layer. Next, a light-emitting layer was formed on the hole-transporting layer to a thickness of 35 nm by co-depositing Compound 2 as the main component of the light-emitting layer and iridium(III)bis(4,6-difluorophenyl)pyridinato-N,C2') picolinate (Flrpic), a blue phosphorescent emitter, as a guest material of the light-emitting layer from different evaporation sources. The concentration of Flrpic was 8.0%. Then, Alq3 was deposited to a thickness of 25 nm as an electron-transporting layer. Further, lithium fluoride (LiF) was deposited on the electron-transporting layer to a thickness of 0.5 nm as an electron-injecting layer. Finally, aluminum (Al) as an electrode was deposited on the electron-injecting layer to a thickness of 170 nm to complete the fabrication of an organic EL device.

The organic EL device thus fabricated was connected to an outside power source and, upon application of direct current voltage, emission of light with the characteristics shown in Table 9 was confirmed. The luminance, voltage, and luminous efficiency in Table 9 are measured at 10 mA/cm$^2$. The maximum wavelength of the spectrum of light emitted from the device is 470 nm and this proves that light is emitted from Flrpic.

Examples 14-21

Organic EL devices were fabricated as in Example 13 with the exception of using respectively Compounds 3, 5, 33, 34, 36, 37, and 38 as the main component of the light-emitting layer. The compounds used as the main component of the light-emitting layer and the luminous characteristics are shown in Table 9.

Comparative Example 2

An organic EL device was fabricated as in Example 13 with the exception of using Compound H-1 as the main component (host material) of the light-emitting layer. The luminous characteristics are shown in Table 9.

TABLE 9

| | Compound | Luminance (cd/m$^2$) | Voltage (V) | Luminous efficiency (lm/W) |
|---|---|---|---|---|
| Example 13 | 2 | 1320 | 9.9 | 4.2 |
| Example 14 | 3 | 1200 | 9.1 | 4.1 |
| Example 15 | 5 | 1150 | 8.8 | 4.1 |
| Example 16 | 33 | 1120 | 9.3 | 3.8 |
| Example 17 | 34 | 1020 | 10.2 | 3.1 |
| Example 19 | 36 | 1270 | 9.2 | 4.3 |
| Example 20 | 37 | 1080 | 9.8 | 3.5 |
| Example 21 | 38 | 1210 | 9.4 | 4.0 |
| Comparative example 2 | H-1 | 925 | 12.8 | 2.3 |

INDUSTRIAL APPLICABILITY

The compound for an organic electroluminescent device of this invention exhibits well-balanced electrical charges injection/transport characteristics and has the lowest triplet excitation energy which is sufficiently high to confine the lowest triplet excitation energy of phosphorescent molecules; hence, the compound is capable of providing an organic EL device which performs at low driving voltage and emits light of high luminance. In addition, the compound shows excellent electrochemical stability and thermal stability and good characteristics in the amorphous state and an organic EL device comprising the compound has excellent driving stability and durability. The organic EL device of this invention is at a level satisfactory for practical use in respect to luminous characteristics, driving life, and durability and is highly valuable technically in applications to flat panel displays (mobile phone display devices, vehicle display devices, office computer display devices, television sets, and the like), light sources utilizing the characteristics of planar light emitters (light sources for illumination and copying machines and backlight sources for liquid crystal displays and instruments), signboards, and beacon lights.

The invention claimed is:

1. A compound for an organic electroluminescent device comprising a compound represented by general formula (2):

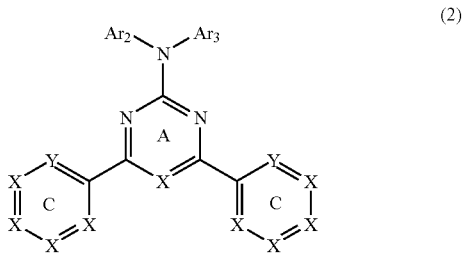

wherein X in ring A is a substituted or unsubstituted methine group or a nitrogen, X and Y in ring C each is independently a substituted or unsubstituted methine group, Ar$_2$ and Ar$_3$ each is independently a substituted or unsubstituted aromatic hydrocarbon group or a substituted or unsubstituted aromatic heterocyclic group; Ar$_2$, Ar$_3$, and the nitrogen to which Ar$_2$ and Ar$_3$ are joined may together form a nitrogen-containing heterocyclic ring.

2. A compound for an organic electroluminescent device as described in claim 1 wherein Ar$_2$ and Ar$_3$ each is independently a phenyl group, a naphthyl group, a phenanthryl group, a pyridyl group, a pyrimidyl group, or a triazyl group in general formula (2).

3. A compound for an organic electroluminescent device as described in claim 1 wherein —NAr$_2$Ar$_3$ is an N-carbazolyl group, an N-phenoxazinyl group, an N-phenothiazinyl group, or an N-β-carbolinyl group in general formula (2).

4. A compound for an organic electroluminescent device as described in claim 1 wherein X in ring A is a nitrogen or an unsubstituted methine group in general formula (2).

5. An organic electroluminescent device comprising an organic layer containing the compound for an organic electroluminescent device described in any one of claims 1, 2, 3 and 4.

6. An organic electroluminescent device as described in claim 5 wherein the aforementioned organic layer is at least one layer selected from a light-emitting layer, a hole-transporting layer, an electron-transporting layer, and a hole-blocking layer.

7. An organic electroluminescent device as described in claim 6 wherein the aforementioned organic layer is the light-emitting layer containing a phosphorescent dopant.

8. A compound for an organic electroluminescent device as described in claim 1 wherein
$Ar_2$, $Ar_3$, and the nitrogen to which $Ar_2$ and $Ar_3$ are joined form a nitrogen-containing heterocyclic ring, wherein the nitrogen-containing heterocyclic ring is a carbazole ring.

* * * * *